United States Patent
Shusta et al.

(10) Patent No.: US 10,233,252 B2
(45) Date of Patent: Mar. 19, 2019

(54) PH-DEPENDENT ANTIBODIES TARGETING THE TRANSFERRIN RECEPTOR AND METHODS OF USE THEREOF TO DELIVER A THERAPEUTIC AGENT

(71) Applicant: Wisconsin Alumni Research Foundation, Madison, WI (US)

(72) Inventors: Eric V. Shusta, Madison, WI (US); Benjamin J. Tillotson, Thousand Oaks, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/379,597

(22) Filed: Dec. 15, 2016

(65) Prior Publication Data
US 2017/0174778 A1    Jun. 22, 2017

Related U.S. Application Data

(60) Provisional application No. 62/270,398, filed on Dec. 21, 2015.

(51) Int. Cl.
*C07K 16/28* (2006.01)

(52) U.S. Cl.
CPC .... *C07K 16/2881* (2013.01); *C07K 2317/565* (2013.01); *C07K 2317/622* (2013.01); *C07K 2317/77* (2013.01); *C07K 2317/92* (2013.01); *C07K 2319/01* (2013.01)

(58) Field of Classification Search
CPC .......... C07K 16/2881; C07K 2317/565; C07K 2317/622; C07K 2317/77; C07K 2317/92; C07K 2319/01
See application file for complete search history.

(56) References Cited

U.S. PATENT DOCUMENTS

2012/0282176 A1* 11/2012 Bohrmann ......... C07K 16/2881
424/1.49

OTHER PUBLICATIONS

Rudikoff S. et al. Proc. Natl. Acad. Sci. USA, 79:1979-1983, 1982.*
Colman, PM. Research in Immunology, Elsevier, NY, 145(1):33-36, 1994.*
Stratagene Catalog. p. 39, 1988.*
Murtaugh ML, et al. (Sep. 2011). Protein Sci. 20(9):1619-31. (doi: 10.1002/pro.696. Epub Aug. 3, 2011).*
Igawa T, et al. (2010). Nature Biotechnology 28:1203-1207. (doi:10.1038/nbt.1691).*
Chapparo-Riggers J, et al. (Mar. 30, 2012). The Journal of Biological Chemistry. 287:11090-11097. (doi:10.1074/jbc.M111.319764. Jan. 31, 2012).*
Atwal, et al. (2011) A Therapeutic Antibody Targeting BACE1 Inhibits Amyloid-β Production in Vivo. Science Translational Medicine 3: 84ra43-84ra43.
Benatuil, et al. (2010) An improved yeast transformation method for the generation of very large human antibody libraries. Protein Engineering Design and Selection 23: 155-159.
Bien-Ly, et al. (2014) Transferrin receptor (TfR) trafficking determines brain uptake of TfR antibody affinity variants. The Journal of Experimental Medicine 211: 233-244.
Boder, et al. (1997) Yeast surface display for screening combinatorial polypeptide libraries. Nat Biotechnol 15: 553-557.
Chan, et al. (2009) Evidence for the adaptation of protein pH-dependence to subcellular pH. BMC Biology 7: 69.
Chaparro-Riggers, et al. (2012) Increasing Serum Half-life and Extending Cholesterol Lowering in Vivo by Engineering Antibody with pH sensitive Binding to PCSK9. Journal of Biological Chemistry 287: 11090-11097.
Chitambar, et al. (1989) Release of soluble transferrin receptor from the surface of human leukemic HL60 cells. Blood 74: 602-608.
Ciechanover, et al. (1983) Kinetics of internalization and recycling of transferrin and the transferrin receptor in a human hepatoma cell line. Effect of lysosomotropic agents. Journal of Biological Chemistry 258: 9681-9689.
Dall'Acqua, et al. (2002) Increasing the Affinity of a Human IgG1 for the Neonatal Fc Receptor: Biological Consequences. The Journal of Immunology 169: 5171-5180.
Dall'Acqua, et al. (2006) Properties of Human IgG1s Engineered for Enhanced Binding to the Neonatal Fc Receptor (FcRn). Journal of Biological Chemistry 281: 23514-23524.
Daniels, et al. (2006) The transferrin receptor part I: Biology and targeting with cytotoxic antibodies for the treatment of cancer Clinical Immunology 121: 144-158.
Daniels, et al. (2006) The transferrin receptor part II: Targeted delivery of therapeutic agents into cancer cells. Clinical Immunology 121: 159-176.
Dautry-Varsat, et al. (1983) pH and the Recycling of Transferrin during Receptor-Mediated Endocytosis. Proceedings of the National Academy of Sciences of the United States of America 80: 2258-2262.
Eckenroth, et al. (2011) How the binding of human transferrin primes the transferrin receptor potentiating iron release at endosomal pH. Proceedings of the National Academy of Sciences of the United States of America 108: 13089-13094.
Edgcomb, et al. (2002) Variability in the pKa of histidine side-chains correlates with burial within proteins. Proteins: Structure, Function, and Bioinformatics 49: 1-6.
Gera, et al. (2012) Design of pH sensitive binding proteins from the hyperthermophilic Sso7d scaffold. PLoS One 7: e48928.

(Continued)

*Primary Examiner* — Robert S Landsman
(74) *Attorney, Agent, or Firm* — Quarles & Brady LLP

(57) ABSTRACT

A pH-dependent antibody that binds an antigen with high affinity at a first pH and rapidly dissociates at a second pH, wherein the antigen is a transferrin receptor (TfR), wherein the association at the second pH/the first pH is less than 20%, and wherein the pH-dependent antibody comprises at least two consecutive histidine residues at a single complementarity determining region (CDR) is disclosed.

28 Claims, 9 Drawing Sheets
(9 of 9 Drawing Sheet(s) Filed in Color)
Specification includes a Sequence Listing.

(56) References Cited

OTHER PUBLICATIONS

Giannetti, et al. (2005) The molecular mechanism for receptor-stimulated iron release from the plasma iron transport protein transferrin. Structure 13: 1613-1623.

Gietz, et al. (2007) High-efficiency yeast transformation using the LiAc/SS carrier DNA/PEG method. Nat Protocols 2: 31-34.

Gumerov, et al. (2003) Interlobe Communication 704 in Human Serum Transferrin: Metal Binding and Conformational Dynamics Investigated by Electrospray Ionization Mass Spectrometry. Biochemistry 42: 5421-5428.

Hackel, et al. (2006) Production of soluble and active transferrin receptor-targeting single-chain antibody using *Saccharomyces cerevisiae*. Pharm Res 23: 790-797.

Igawa, et al. (2010) Antibody recycling by engineered pH-dependent antigen binding improves the duration of antigen neutralization. Nat Biotech 28: 1203-1207.

Kulkarni, et al. (2010) Two Independent Histidines, One in Human Prolactin and One in Its Receptor, Are Critical for pH-dependent Receptor Recognition and Activation. Journal of Biological Chemistry 285: 38524-38533.

Lao, et al. (2007) Inhibition of transferrin iron release increases in vitro drug carrier efficacy. Journal of Controlled Release 117: 403-412.

Leverence, et al. (2010) Noncanonical interactions between serum transferrin and transferrin receptor evaluated with electrospray ionization mass spectrometry. Proceedings of the National Academy of Sciences 107: 8123-8128.

Luck, et al. (2013) Structure and dynamics of drug carriers and their interaction with cellular receptors: Focus on serum transferrin. Advanced Drug Delivery Reviews 65: 1012-1019.

Martin, et al. (2001) Crystal Structure at 2.8 Å of an FcRn/Heterodimeric Fc Complex: Mechanism of pH-Dependent Binding. Molecular Cell 7: 867-877.

Mayle, et al. (2012) The intracellular trafficking pathway of transferrin. Biochimica et Biophysica Acta (BBA)—General Subjects 1820: 264-281.

Murtaugh, et al. (2011) A combinatorial histidine scanning library approach to engineer highly pH-dependent protein switches. Protein Sci 20: 1619-1631.

Niewoehner, et al. (2014) Increased Brain Penetration and Potency of a Therapeutic Antibody Using a Monovalent Molecular Shuttle. Neuron 81: 49-60.

Oganesyan, et al. (2009) Structural characterization of a human Fc fragment engineered for extended serum half-life. Molecular Immunology 46: 1750-1755.

Piatesi, et al. (2006) Directed evolution for improved secretion of cancer—testis antigen NY-ESO-1 from yeast. Protein Expression and Purification 48: 232-242.

Poul, et al. (2000) Selection of tumor-specific internalizing human antibodies from phage libraries. Journal of Molecular Biology 301: 1149-1161.

Roopenian, et al. (2007) FcRn: the neonatal Fc receptor comes of age. Nat Rev Immunol 7: 715-725.

Sade, et al. (2014) A Human Blood-Brain Barrier Transcytosis Assay Reveals Antibody Transcytosis Influenced by pH-Dependent Receptor Binding. PLoS One 9: e96340.

Sarkar, et al. (2002) Rational cytokine design for increased lifetime and enhanced potency using pH-activated [ldquo] histidine switching[rdquo]. Nat Biotech 20: 908-913.

Schröter, et al.(2014) A generic approach to engineer antibody pH-switches using combinatorial histidine scanning libraries and yeast display. mAbs 7: 138-151.

Shusta, et al. (1998) Increasing the secretory capacity of *Saccharomyces cerevisiae* for production of single-chain antibody fragments. Nat Biotech 16: 773-777. SCAN.

Sun, et al.(1998) [1H, 13C] NMR determination of the order of lobe loading of human transferrin with iron: comparison with other metal ions. FEBS Letters 422: 315-320.

Swers, et al.(2004) Shuffled antibody libraries created by in vivo homologous recombination and yeast surface display. Nucleic Acids Research 32: e36-e36.

Tillotson, et al. (2013) Antibody affinity maturation using yeast display with detergent-solubilized membrane proteins as antigen sources. Protein Engineering Design and Selection 26: 101-112.

Traxlmayr, et al. (2014) Construction of pH-sensitive Her2-binding IgG1-Fc by directed evolution. Biotechnology Journal 9: 1013-1022.

Vaccaro, et al. (2005) Engineering the Fc region of immunoglobulin G to modulate in vivo antibody levels. Nat Biotech 23: 1283-1288.

Van Antwerp, et al. (2000) Fine Affinity Discrimination by Yeast Surface Display and Flow Cytometry. Biotechnology Progress 16: 31-37.

Wally, et al. (2006) The Crystal Structure of Iron-free Human Serum Transferrin Provides Insight into Inter-lobe Communication and Receptor Binding. Journal of Biological Chemistry 281: 24934-24944.

Wang, et al. (2007) Mining a yeast library for brain endothelial cell-binding antibodies. Nat Methods 4: 143-145.

Wenning, et al. (1998) Quantitative analysis of protein synthesis inhibition and recovery in CRM107 immunotoxin-treated HeLa cells. Biotechnology and Bioengineering 57: 484-496.

Wentz, et al. (2007) A Novel High-Throughput Screen Reveals Yeast Genes That Increase Secretion of Heterologous Proteins. Applied and Environmental Microbiology 73: 1189-1198.

Yazdi, et al. (1994) Quantitative Analysis of Protein Synthesis Inhibition by Transferrin-Toxin Conjugates. Cancer Research 54: 6387-6394.

Yazdi, et al. (1995) Influence of Cellular Trafficking on Protein Synthesis Inhibition of Immunotoxins Directed against the Transferrin Receptor. Cancer Research 55: 3763-3771.

Yoon, et al. (2009) Genetically engineering transferrin to improve its in vitro ability to deliver cytotoxins. Journal of Controlled Release 133: 178-184.

Yu, et al. (2011) Boosting Brain Uptake of a Therapeutic Antibody by Reducing Its Affinity for a Transcytosis Target. Science Translational Medicine 3: 84ra44-84ra44.

\* cited by examiner (a)

(b)

(c)

SEQUENCE LISTING

```
<160> NUMBER OF SEQ ID NOS: 37

<210> SEQ ID NO 1
<211> LENGTH: 10
<212> TYPE: PRT
<213> ORGANISM: Artificial Sequence
<220> FEATURE:
<223> OTHER INFORMATION: LD1 - Randomly selected clones from CDRH1his

<400> SEQUENCE: 1
```

Arg Phe Pro Leu Ser His His Asp Ile His
1               5                   10

<210> SEQ ID NO 2
<211> LENGTH: 10
<212> TYPE: PRT
<213> ORGANISM: Artificial Sequence
<220> FEATURE:
<223> OTHER INFORMATION: LD2 - Randomly selected clones from CDRH1his

<400> SEQUENCE: 2

Arg Phe His His Ser Arg Tyr Asp Met His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: LD3 - Randomly selected clones from CDRH1his

<400> SEQUENCE: 3

Arg Tyr Thr Phe His Arg Tyr Ala Lys His
1               5                   10

<210> SEQ ID NO 4
<211> LENGTH: 10
<212> TYPE: PRT
<213> ORGANISM: Artificial Sequence
<220> FEATURE:
<223> OTHER INFORMATION: LD4 - Randomly selected clones from CDRH1his

<400> SEQUENCE: 4

Arg Tyr Asn Tyr Arg Arg Tyr Asp Ile His
1               5                   10

<210> SEQ ID NO 5
<211> LENGTH: 10
<212> TYPE: PRT
<213> ORGANISM: Artificial Sequence
<220> FEATURE:
<223> OTHER INFORMATION: LD5 - Randomly selected clones from CDRH1his

<400> SEQUENCE: 5

Gln Phe Thr Tyr Asn Arg His Pro Met His
1               5                   10

<210> SEQ ID NO 6
<211> LENGTH: 10
<212> TYPE: PRT
<213> ORGANISM: Artificial Sequence
<220> FEATURE:
<223> OTHER INFORMATION: LD6 - Randomly selected clones from CDRH1his

<400> SEQUENCE: 6

His Tyr His Leu Ser Ser Tyr His Leu His
1               5                   10

<210> SEQ ID NO 7
<211> LENGTH: 10
<212> TYPE: PRT
<213> ORGANISM: Artificial Sequence
<220> FEATURE:
<223> OTHER INFORMATION: LD7 - Randomly selected clones from CDRH1his

<400> SEQUENCE: 7

Arg Phe Asn Leu Asn His His His His

```
<210> SEQ ID NO 8
<211> LENGTH: 10
<212> TYPE: PRT
<213> ORGANISM: Artificial Sequence
<220> FEATURE:
<223> OTHER INFORMATION: LD8 - Randomly selected clones from CDRH1his

<400> SEQUENCE: 8

His His Asn His Arg Asn Tyr Ala Asn His
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: LD9 - Randomly selected clones from CDRH1his

<400> SEQUENCE: 9

Arg Tyr Pro Phe Ser Ser Tyr His Leu His
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: LD10 - Randomly selected clones from CDRH1his

<400> SEQUENCE: 10

Arg Phe Thr Tyr Asn Ser Tyr Ala Lys His
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: LD11 - Randomly selected clones from CDRH1his

<400> SEQUENCE: 11

Arg Phe Thr Thr Ser His His Pro His His
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: LD12 - Randomly selected clones from CDRH1his

<400> SEQUENCE: 12

Arg His Thr Phe Ser Ser Tyr Ala His His
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: M4 - CDRH1 mutant with increased dissociation
       at pH5.5

<400> SEQUENCE: 13

Arg Leu Asn Tyr Asn Ser His His Met His
```

```
<210> SEQ ID NO 14
<211> LENGTH: 10
<212> TYPE: PRT
<213> ORGANISM: Artificial Sequence
<220> FEATURE:
<223> OTHER INFORMATION: M8 - CDRH1 mutant with increased dissociation
      at pH5.5

<400> SEQUENCE: 14

His Tyr Asn Tyr Ser Asn Tyr Pro Met His
1               5                   10

<210> SEQ ID NO 15
<211> LENGTH: 10
<212> TYPE: PRT
<213> ORGANISM: Artificial Sequence
<220> FEATURE:
<223> OTHER INFORMATION: M10 - CDRH1 mutant with increased dissociation
      at pH5.5

<400> SEQUENCE: 15

His Leu His His Asn His His Pro Leu His
1               5                   10

<210> SEQ ID NO 16
<211> LENGTH: 10
<212> TYPE: PRT
<213> ORGANISM: Artificial Sequence
<220> FEATURE:
<223> OTHER INFORMATION: M11 - CDRH1 mutant with increased dissociation
      at pH5.5

<400> SEQUENCE: 16

Arg Leu Asn Phe His His His Ala Met His
1               5                   10

<210> SEQ ID NO 17
<211> LENGTH: 10
<212> TYPE: PRT
<213> ORGANISM: Artificial Sequence
<220> FEATURE:
<223> OTHER INFORMATION: M16 - CDRH1 mutant with increased dissociation
      at pH5.5

<400> SEQUENCE: 17

Arg Tyr Pro Phe His His His Asp His His
1               5                   10

<210> SEQ ID NO 18
<211> LENGTH: 10
<212> TYPE: PRT
<213> ORGANISM: Artificial Sequence
<220> FEATURE:
<223> OTHER INFORMATION: M17 - CDRH1 mutant with increased dissociation
      at pH5.5

<400> SEQUENCE: 18

Arg Phe His His His Arg Tyr Ala Gln His
1               5                   10

<210> SEQ ID NO 19
<211> LENGTH: 10
<212> TYPE: PRT
<213> ORGANISM: Artificial Sequence
<220> FEATURE:
<223> OTHER INFORMATION: M20 - CDRH1 mutant with increased dissociation
``` at pH5.5

<400> SEQUENCE: 19

Arg Phe Pro Phe His His His Pro Ile His
1               5                   10

<210> SEQ ID NO 20
<211> LENGTH: 10
<212> TYPE: PRT
<213> ORGANISM: Artificial Sequence
<220> FEATURE:
<223> OTHER INFORMATION: M23 - CDRH1 mutant with increased dissociation
      at pH5.5

<400> SEQUENCE: 20

Arg Phe Ser Phe His His His Pro Ile His
1               5                   10

<210> SEQ ID NO 21
<211> LENGTH: 10
<212> TYPE: PRT
<213> ORGANISM: Artificial Sequence
<220> FEATURE:
<223> OTHER INFORMATION: N4 - CDRH1 mutant with reduced dissociation at
      pH5.5

<400> SEQUENCE: 21

Arg Phe His Phe Asn Arg Tyr His Met His
1               5                   10

<210> SEQ ID NO 22
<211> LENGTH: 10
<212> TYPE: PRT
<213> ORGANISM: Artificial Sequence
<220> FEATURE:
<223> OTHER INFORMATION: N5 - CDRH1 mutant with reduced dissociation at
      pH5.5

<400> SEQUENCE: 22

Arg Phe Thr Phe Asn Asn Tyr Ala Met His
1               5                   10

<210> SEQ ID NO 23
<211> LENGTH: 10
<212> TYPE: PRT
<213> ORGANISM: Artificial Sequence
<220> FEATURE:
<223> OTHER INFORMATION: N7 - CDRH1 mutant with reduced dissociation at
      pH5.5

<400> SEQUENCE: 23

Arg His His Leu Ser Ser Tyr Asp Met His
1               5                   10

<210> SEQ ID NO 24
<211> LENGTH: 10
<212> TYPE: PRT
<213> ORGANISM: Artificial Sequence
<220> FEATURE:
<223> OTHER INFORMATION: N10 - CDRH1 mutant with reduced dissociation at
      pH5.5

<400> SEQUENCE: 24

Arg Phe His Leu Asn Ser Tyr Asp Met His
1               5                   10

<210> SEQ ID NO 25

```
<211> LENGTH: 10
<212> TYPE: PRT
<213> ORGANISM: Artificial Sequence
<220> FEATURE:
<223> OTHER INFORMATION: 5P4 - CDRH1 mutant with reduced dissociation at
      pH5.5

<400> SEQUENCE: 25

Gln Phe His Phe Asn Asn Tyr Asp Leu His
1               5                   10

<210> SEQ ID NO 26
<211> LENGTH: 10
<212> TYPE: PRT
<213> ORGANISM: Artificial Sequence
<220> FEATURE:
<223> OTHER INFORMATION: 5P7 - CDRH1 mutant with reduced dissociation at
      pH5.5

<400> SEQUENCE: 26

Arg Phe Thr Phe Ser His Tyr Asp Leu His
1               5                   10

<210> SEQ ID NO 27
<211> LENGTH: 10
<212> TYPE: PRT
<213> ORGANISM: Artificial Sequence
<220> FEATURE:
<223> OTHER INFORMATION: 5P9 - CDRH1 mutant with reduced dissociation at
      pH5.5

<400> SEQUENCE: 27

Arg Phe Thr Phe Ser Asn Tyr His His His
1               5                   10

<210> SEQ ID NO 28
<211> LENGTH: 10
<212> TYPE: PRT
<213> ORGANISM: Artificial Sequence
<220> FEATURE:
<223> OTHER INFORMATION: 5P15 - CDRH1 mutant with reduced dissociation a
      t pH5.5

<400> SEQUENCE: 28

Gln His Asn Leu Arg Ser Tyr His Leu His
1               5                   10

<210> SEQ ID NO 29
<211> LENGTH: 45
<212> TYPE: DNA
<213> ORGANISM: Artificial Sequence
<220> FEATURE:
<223> OTHER INFORMATION: primers H7sdmF

<400> SEQUENCE: 29
gcctctcgat tcaccttcac tagttaataa atgcactggg tccgc              45

<210> SEQ ID NO 30
<211> LENGTH: 51
<212> TYPE: DNA
<213> ORGANISM: Artificial Sequence
<220> FEATURE:
<223> OTHER INFORMATION: Primer H7sdmR

<400> SEQUENCE: 30
ctggcggacc cagtgcattt attaactagt gaaggtgaat cgagaggcca g        51
```

<210> SEQ ID NO 31
<211> LENGTH: 25
<212> TYPE: DNA
<213> ORGANISM: Artificial Sequence
<220> FEATURE:
<223> OTHER INFORMATION: primer BTSeqF

<400> SEQUENCE: 31
ctgctccgaa caataaagat tctac                                         25

<210> SEQ ID NO 32
<211> LENGTH: 25
<212> TYPE: DNA
<213> ORGANISM: Artificial Sequence
<220> FEATURE:
<223> OTHER INFORMATION: Primer BTSeqR

<400> SEQUENCE: 32
gtatgtgtaa agttggtaac ggaac                                         25

<210> SEQ ID NO 33
<211> LENGTH: 90
<212> TYPE: DNA
<213> ORGANISM: Artificial Sequence
<220> FEATURE:
<223> OTHER INFORMATION: IP90T - S = G/C, R = A/G, Y = C/T, K = G/T, M =
     A/C, W = A/T

<400> SEQUENCE: 33
aggtccctga gactctcctg tgcagcctct crwywcmmcy wcmrtmrcya tsmtmwkcac    60
tgggtccgcc aggctccagg caaggggctg                                    90

<210> SEQ ID NO 34
<211> LENGTH: 28
<212> TYPE: DNA
<213> ORGANISM: Artificial Sequence
<220> FEATURE:
<223> OTHER INFORMATION: primer IPCDH1ampF

<400> SEQUENCE: 34
ccacccactc cagccccttg cctggagc                                      28

<210> SEQ ID NO 35
<211> LENGTH: 33
<212> TYPE: DNA
<213> ORGANISM: Artificial Sequence
<220> FEATURE:
<223> OTHER INFORMATION: Primer IPCDH1ampR

<400> SEQUENCE: 35
ccagcctggg aggtccctga gactctcctg tgc                                33

<210> SEQ ID NO 36
<211> LENGTH: 120
<212> TYPE: PRT
<213> ORGANISM: Artificial Sequence
<220> FEATURE:
<223> OTHER INFORMATION: scFv H7 heavy chain protein sequence

<400> SEQUENCE: 36

Gln Val Gln Leu Gln Glu Ser Gly Gly Gly Val Val Gln Pro Gly Arg
1               5                   10                  15

Ser Leu Arg Leu Ser Cys Ala Ala Ser Arg Phe Thr Phe Ser Ser Tyr
            20                  25                  30

Ala Met His Trp Val Arg Gln Ala Pro Gly Lys Gly Leu Glu Trp Val

```
                    35                  40                  45
Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Gly Tyr Gly Asp Tyr Pro Asp Tyr Trp Gly Gln
            100                 105                 110

Gly Thr Leu Val Thr Val Ser Ser
            115                 120

<210> SEQ ID NO 37
<211> LENGTH: 108
<212> TYPE: PRT
<213> ORGANISM: Artificial Sequence
<220> FEATURE:
<223> OTHER INFORMATION: scFv H7 light chain protein sequence

<400> SEQUENCE: 37

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Met Tyr Gly
        35                  40                  45

Arg Asn Glu Arg Pro Ser Gly Val Pro Asp Arg Phe Ser Gly Ser Lys
50                  55                  60

Ser Gly Thr Ser Ala Ser Leu Ala Ile Ser Gly Leu Gln Pro Glu Asp
65                  70                  75                  80

Glu Ala Asn Tyr Tyr Cys Ala Gly Trp Asp Asp Ser Leu Thr Gly Pro
                85                  90                  95

Val Phe Gly Gly Gly Thr Lys Leu Thr Val Leu Gly
            100                 105
```

PH-DEPENDENT ANTIBODIES TARGETING THE TRANSFERRIN RECEPTOR AND METHODS OF USE THEREOF TO DELIVER A THERAPEUTIC AGENT

CROSS REFERENCE TO RELATED APPLICATIONS

This application claims the benefit of U.S. Provisional Patent Application No. 62/270,398, filed on Dec. 21, 2015, which was incorporated by reference herein in its entirety for all purpose.

STATEMENT REGARDING FEDERALLY SPONSORED RESEARCH/DEVELOPMENT

This invention was made with government support under NS071513 awarded by the National Institutes of Health. The government has certain rights in the invention.

BACKGROUND

Drug delivery to the brain is hampered by the presence of the blood-brain barrier (BBB). The BBB endothelium is very impermeable and allows only those molecules that have combined properties of low molecular weight (<500 Da) and lipophilicity to enter the brain from the bloodstream. Even molecules with such attributes may be effluxed as substrates for p-glycoprotein or similar transporters. Taken together, these BBB properties conspire to restrict BBB passage of greater than 98% of small molecule pharmaceuticals and nearly 100% of all protein and gene therapeutics. However, if antibodies are used to target receptor-mediated transport systems at the BBB, drug molecules and drug carriers can be effectively transcytosed across the BBB endothelium into brain tissue. Such noninvasive delivery from blood to brain is a result of the antibody acting as a surrogate ligand for the endogenous transport systems. Current known antibody-targeted brain delivery systems include the transferrin and insulin receptor systems. These are expressed ubiquitously throughout the body and lead to mis-targeting of expensive pharmaceuticals.

Receptor-ligand recognition and binding frequently depend on pH-induced changes stemming from the combined protonation states of amino acids within the protein. Histidine is considered a key amino acid driving pH sensitivity having a side-chain pKa of 5.5-6.5 in the context of proteins [1]. Evidence suggests that proteins have adapted to function in a range of subcellular pH environments through non-random placement of histidine residues [2]. These phenomena have been exploited in therapeutic protein design to alter intracellular trafficking. For example, interactions with the neonatal Fc-receptor (FcRn), which functions in a pH dependent manner to regulate serum IgG levels [3], have been modified. The Fc region surrounding critical histidine residues of the monoclonal antibody Motavizumab was mutated improving FcRn binding at pH 6.0 without affecting its affinity at pH 7.2, thereby achieving a 4-fold extension in serum half-life [4-6]. In contrast, desiring a reduction in therapeutic IgG serum half-life, a competitive antibody, or "Abdeg", was created to bind FcRn tightly at both pH 6.0 and pH 7.2, hence occupying FcRn at the expense of therapeutic antibody binding [7]. While these studies describe the modulation of a preexisting pH-dependent system, it is also possible to introduce pH-sensitive binding. As examples, both the anti-IL6R antibody Tocilizumab [8], and the anti-PCSK9 antibody RN316 [9] were engineered to escape target-mediated degradation by introducing histidine residues at select positions in the antibody CDR loops, so as to induce antibody-antigen dissociation at endosomal pH. Engineering pH-sensitive ligand binding has also been employed to increase the potency of non-immunoglobulin scaffolds as in the case of the cytokine GCSF [10], and the iron carrier protein transferrin [11].

The transferrin receptor (TfR) presents a valuable therapeutic target which can be antagonized directly, or exploited indirectly as an intracellular drug delivery vector. These opportunities result from the ubiquitous expression of TfR on normal cells and elevated expression on cancer cells, as well as the endocytotic route used to transport iron-bearing transferrin inside the cell (reviewed in [12,13]). The natural ligand for TfR, the serum protein transferrin (Tf), circulates in iron-free (apoTf) or iron-bound (holoTf) forms [14,15]. HoloTf binds the transferrin receptor (TfR) tightly at blood pH (7.2-7.4), and the complex is internalized via clathrin-mediated endocytosis (CME) [16]. As holoTf-TfR complexes cycle though acidic endosomes (pH 5.0-6.0), an intricately coordinated series of pH-induced conformational changes induces the release of both iron molecules to yield apoTf, which has an increased affinity for TfR at endosomal pH [15,17-19]. This is followed by recycling of the apoTf-TfR complex to the cell surface (pH 7.2-7.4) where apoTf has a decreased affinity for TfR and dissociates back into the blood stream [17,20]. Cytotoxins based on conjugates of transferrin have been widely studied as therapeutic agents [21]. A detailed kinetic model of the TfR cycle was created and analyzed for routes that might lead to a greater overall cellular association of Tf or Tf conjugates [11]. It was posited that inhibition of iron release from Tf could lead to endosomal dissociation of holoTf that, unlike apoTf, could rapidly rebind at blood pH and participate in further cycles of endocytosis at blood pH [11,17]. Indeed, when Tf was genetically altered to inhibit iron release, diphtheria toxin conjugates of the mutant Tf showed increased cytotoxicity compared to wild-type Tf conjugates [22]. Similarly, it has been shown that improved cytotoxin efficacy for Tf conjugates as well as anti-TfR antibodies is a direct result of increased cellular association [23-25].

Needed in the art is an antibody with pH-sensitive binding capability. Specifically, needed in the art are anti-TfR antibodies that bind TfR in a pH-dependent manner. For example, the needed antibodies could bind TfR at physiological pH and could release TfR rapidly at endosomal pH.

SUMMARY OF THE INVENTION

In one embodiment, the present invention is a pH-dependent antibody that binds an antigen with higher affinity at a first pH than at a second pH, wherein the antigen is a transferrin receptor (TfR). These antibodies will be useful in enhancing an increase in antibody accumulation, preferably linked to a therapeutic agent, across a blood brain barrier or a cellular membrane. In a preferred embodiment, the increase in accumulation of the antibody is at least 2 fold, preferably at least 2.6 fold. In another embodiment, the association of the antibody with the antigen at the second pH versus the first pH is less than 20%.

In a preferred embodiment the pH-dependent antibody comprises at least two consecutive histidine residues at a single complementarity determining region (CDR). In some preferred embodiments, the CDR is CDRH1. In some preferred embodiments, the pH-dependent antibody comprises at least three consecutive histidine residues.

In some embodiments of the present invention, the pH-dependent antibody comprises an antibody fragment having an amino acid sequence selected from the group consisting of SEQ ID NOs 13-20 (corresponding to M4, M8, M10, M11, M16, M17, M20 and M23). In some embodiments, the pH-dependent antibody comprises an antibody fragment having an amino acid sequence of SEQ ID NO:17 (corresponding to M16).

In some embodiments, the present invention is a method of delivering a therapeutic agent into a cell, preferably a cancer cell. In one embodiment the method comprises the steps of (a) obtaining a pH-dependent antibody according to the present invention; (b) exposing the cell to an effective amount of the pH-dependent antibody; and (c) exposing the cell to an effective amount of the agent, wherein the agent is delivered to the cell in an enhanced manner. In preferred embodiments, the cell is exposed to the agent at the same time as the cell is exposed to the pH-dependent antibody. In a preferred embodiment, the cell is a cancer cell.

In some embodiments, the present invention is a method of delivering a therapeutic agent through a blood-brain barrier (BBB) of a subject, the method comprising the steps of (a) obtaining a pH-dependent antibody according to the present invention; (b) exposing the BBB of the subject to a pharmaceutically effective amount of the pH-dependent antibody; and (c) exposing the BBB of the subject to a pharmaceutically effective amount of the agent, wherein the agent is delivered though the BBB. In preferred embodiments, the BBB of the subject is exposed to the agent at the same time as the BBB being exposed to the pH-dependent antibody.

In some embodiments, the present invention is a vector comprising a pH-dependent antibody or a microorganism comprising the vector.

In some embodiments, the present invention is a kit for delivering a molecule through a blood-brain barrier (BBB) or cancer cell of a subject, the kit comprising a pH-dependent antibody of the present invention.

DESCRIPTION OF DRAWINGS

This patent application file contains at least one drawing executed in color. Copies of this patent or patent application publication with color drawings will be provided by the Office upon request and payment of the necessary fee.

FIGS. 1(A and B) is a set of diagrams showing creation and screening methodology for a histidine-saturated CDRH1 library based on the wild-type anti-TfR scFv, H7.

FIG. 2 (A-H) is a set of graphs showing flow-cytometric screening of the CDRH1his library for scFvs having affected dissociation from TfR at pH 5.5. Dot plots depict the behavior of the various scFv populations after saturation with rhTfR followed by a 10 minute dissociation step in pH 5.5 or 7.4 buffers. TfR-binding is indicated on the y-axis while scFv surface expression level is indicated on the x-axis. Sample gates are drawn only for illustrative purposes for the reader to follow the sorting enrichment procedure. FIG. 2A: Antigen binding and expression of wild-type H7 at pH 7.4. FIG. 2B and FIG. 2D: Pool F was derived from the CDRH1his library via two rounds of sorting at pH 7.4 and comprises neutral pH TfR-binders. FIG. 2C (also FIG. 7): A population comprising pH-insensitive binders exists in CDRH1his and can be visualized in gate F after the library is subject to pH 5.5 dissociation. FIG. 2E: Antigen binding and expression of wild type H7 at pH 5.5. FIG. 2F: Both pools M and N were obtained by selecting for different populations within pool F, post dissociation at pH 5.5. FIG. 2F and FIG. 2G: Gate N was placed near the maximum in TfR-binding signal to select for pH-insensitive scFvs and ultimately yielded pool N. FIG. 2F and FIG. 2H: Alternatively, gate M was placed just above the no-antigen control, but below gate N to select for the pH-sensitive binders ultimately found in pool M (FIG. 7). FIG. 2G and FIG. 2H: Flow-cytometric analysis of the M and N pools. Individual clones arising from these screening strategies are listed in Table 1 and quantitative clonal dissociation behavior is shown in FIG. 3. Further detailed explanation of the screening strategy and pools depicted in the various panels can be found in the text.

FIG. 3(A-C) is a set of graphs showing quantitative analysis of scFvs isolated from the CDRH1his library using yeast surface display.

FIGS. 4(A and B) is a set of graphs and images showing analysis of soluble M16, N5 and H7 scFvs.

FIGS. 5(A, B and C) is a set of graphs and images showing endocytosis of scFvs into SK-BR-3 cells and quantification of intracellular accumulation.

FIG. 6(A-D) is a set of graphs and images showing intracellular co-localization of scFvs with endosomal and lysosomal markers.

FIG. 7(A-C) is a set of graphs showing flow cytometric screening of the CDRH1his library for scFvs lacking pH 5.5 sensitivity.

DESCRIPTION OF THE INVENTION

In General

Figures 1A, 1B:
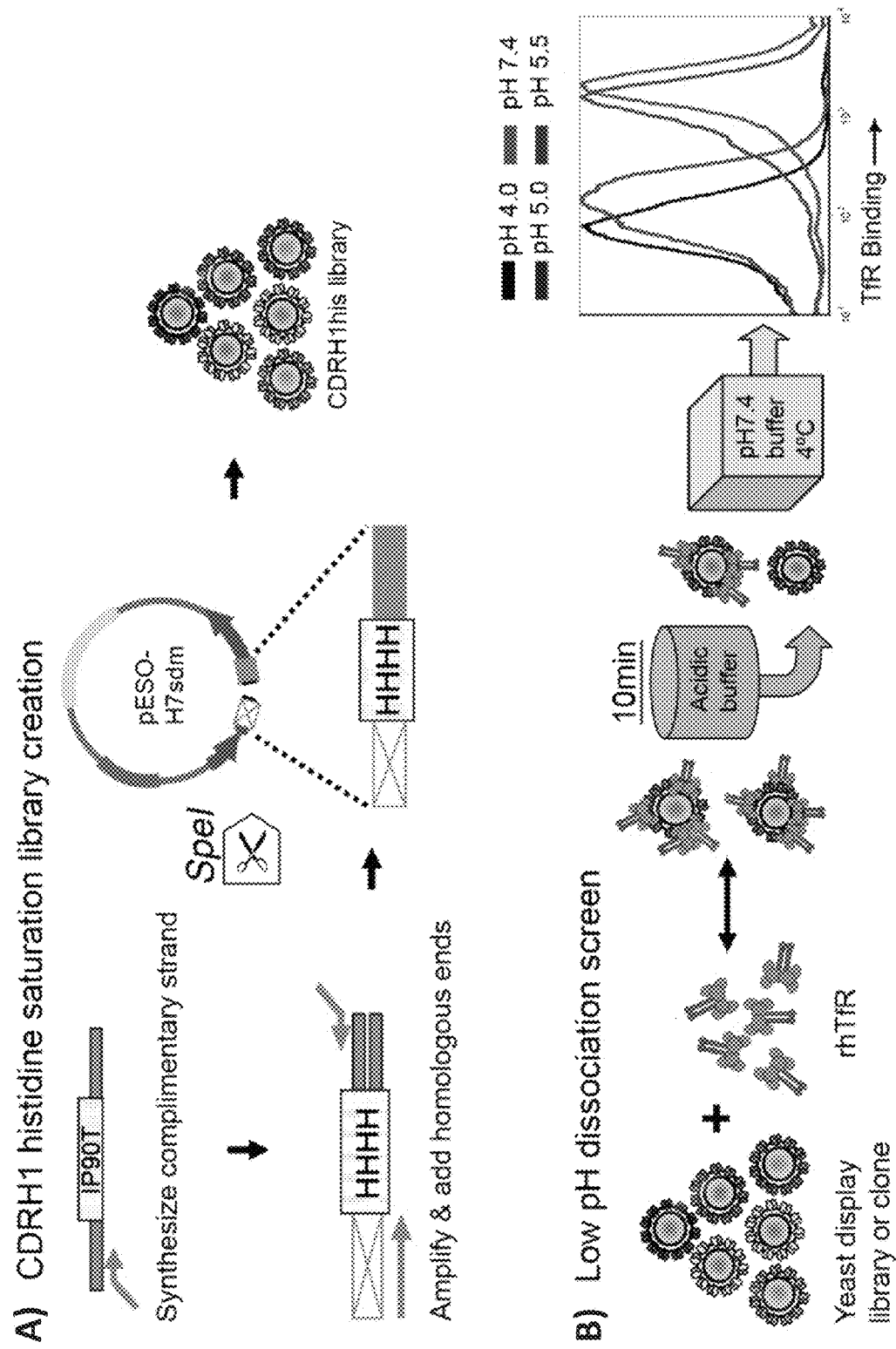
FIG. 1A: The pESO-H7sdm vector contained a mutant scFv H7, that was specially designed to harbor a unique restriction site (SpeI) followed by two stop codons in CDRH1. SpeI digestion of pESO-H7sdm produced a linearized backbone that would be undetectable by flow cytometry if introduced as a reclosed vector into yeast (no c-myc epitope tag expression as a result of the double stop codon). A double-stranded DNA cassette containing the histidine-saturated CDRH1 was built using two cycles of PCR, from primers and a degenerate oligonucleotide (IP90T). Although depicted as a single entity for simplicity, IP90T was in fact a mixture of millions of unique ssDNA oligos representing all possible combinations of histidine in CDRH1. The CDRH1his cassette and linearized pESO-H7sdm were used to create the CDRH1his library by homologous recombination in yeast.
FIG. 1B: Screening and assessment of yeast-displayed scFvs was accomplished by saturating with recombinant human transferrin receptor (rhTfR) followed by a 10 minute incubation in acidic buffer (pH 4.0-6.5) and assay for TfR dissociation. A pH 5.5 buffer was used to simulate endosomal conditions relevant to transferrin-TfR dissociation [19,20]. A dissociation control was included by using a pH 7.4 buffer as opposed to acidic buffer at this step. The dissociation process was halted by addition of an excess volume of ice cold pH 7.4 buffer. Surface constructs were subsequently immunolabeled and analyzed by flow cytometry. The histogram depicts the response of yeast-displayed wild-type scFv H7 to 10 minute incubation with buffers having acidic pH.

Before the present invention is described, it is understood that this invention is not limited to the particular methodology, protocols, and reagents described, as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As used herein "subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In one specific embodiment, a subject is a human being.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, intradermal administration and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" or "exposing," as used herein refers to bringing a disclosed compound and a cell, a target receptor, or other biological entity together in such a manner that the compound can affect the activity of the target (e.g., enzyme, cell, etc.), either directly; i.e., by interacting with the target itself, or indirectly; i.e., by interacting with another molecule, co-factor, factor, or protein on which the activity of the target is dependent.

As used herein, "pharmaceutical composition" means therapeutically effective amounts of the BBB transcytosis compound (also termed "pharmaceutically active compound") together with suitable diluents, preservatives, solubilizers, emulsifiers, and adjuvants, collectively "pharmaceutically-acceptable carriers." As used herein, the terms "effective amount" and "therapeutically effective amount"

refer to the quantity of active therapeutic agent or agents sufficient to yield a desired therapeutic response without undue adverse side effects such as toxicity, irritation, or allergic response. The specific "effective amount" will, obviously, vary with such factors as the particular condition being treated, the physical condition of the subject, the type of animal being treated, the duration of the treatment, the nature of concurrent therapy (if any), and the specific formulations employed and the structure of the compounds or its derivatives. In one embodiment, an amount would be deemed therapeutically effective if it resulted in one or more of the following: (a) the prevention of a neurological or brain disease (e. g., Alzheimer, Parkinson's and/or cancer); and (b) the reversal or stabilization of a neurological or brain disease (e.g., Alzheimer, Parkinson's and/or cancer). The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e. g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Further, as used herein "pharmaceutically acceptable carriers" are well known to those skilled in the art and include, but are not limited to, 0.01-0.1M and preferably 0.05M phosphate buffer or 0.9% saline. Additionally, such pharmaceutically acceptable carriers may be aqueous or non-aqueous solutions, suspensions, and emulsions. Examples of nonaqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

For purposes of the present invention, "treating" or "treatment" describes the management and care of a subject for the purpose of combating the disease, condition, or disorder. The terms embrace both preventive, i.e., prophylactic, and palliative treatment as well as therapeutic treatment. Treating includes the administration of a compound of present invention to prevent the onset of the symptoms or complications, alleviating the symptoms or complications, or eliminating the disease, condition, or disorder.

The term "antibody" or "antibody molecule" as used herein refers to immunoglobulin molecules or other molecules which comprise an antigen binding domain. The term "antibody" or "antibody molecule" as used herein is thus intended to include whole antibodies (e.g., IgG, IgA, IgE, IgM, or IgD), monoclonal antibodies, polyclonal antibodies, and chimeric antibodies.

The terms "monoclonal antibody" or "monoclonal antibody composition" as used herein refer to a preparation of antibody molecules of a single amino acid composition. The monoclonal antibody also includes "human monoclonal antibody" which refers to antibodies displaying a single binding specificity which have variable and constant regions derived from human germline immunoglobulin sequences. The human monoclonal antibodies can be produced by a hybridoma which includes a B cell obtained from a transgenic nonhuman animal, for example, a transgenic mouse, having a genome comprising a human heavy chain transgene and a light human chain transgene fused to an immortalized cell.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies can also comprise a murine variable region and a human constant region. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art.

The term "antibody" also shall include humanized antibody, human antibody and recombinant human antibody. The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." Particularly preferred CDRs correspond to those representing sequences recognizing the antigens noted above for chimeric and bifunctional antibodies.

The term "human antibody" includes antibodies having variable and constant regions derived from human germline immunoglobulin sequences. The variable heavy chain is preferably derived from germline sequence DP-50 and the variable light chain is derived from germline sequence L6. The constant regions of the antibody are constant regions of human IgG 1 type.

The term "recombinant human antibody" includes all human antibodies that are prepared, expressed, created or isolated by recombinant means, such as antibodies isolated from a host cell such as an SP2-0, NS0 or CHO cell (like CHO K1) or from an animal (e.g., a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form.

The term "antibody" also includes "antibody fragments" or "antibody-derived fragments" which comprise an antigen binding domain. The term "antibody fragment" as used herein is intended to include any appropriate antibody fragment that displays antigen binding function, for example, Fab, Fab', F(ab')2, scFv, Fv, dsFv, ds-scFv, Fd, dAbs, TandAbs dimers, mini bodies, monobodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art.

The antibodies or antibody fragments can be produced naturally or can be wholly or partially synthetically produced. Thus the antibody may be from any appropriate source, for example recombinant sources and/or produced in transgenic animals or transgenic plants. Thus, the antibody molecules can be produced in vitro or in vivo. Preferably the antibody or antibody fragment comprises an antibody light chain variable region ($V_L$) and an antibody heavy chain variable region ($V_H$) which generally comprise the antigen binding site. The antibody or antibody fragment can comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region. Furthermore, the antibody or antibody fragment can comprise all or a portion of a kappa light chain constant region or a lambda light chain constant region. All or part of such constant regions may be produced naturally or may be wholly or partially synthetic. Appropriate sequences for such constant regions are well known and documented in the art.

The term "fragment" as used herein refers to fragments of biological relevance (functional fragment), e.g., fragments which can contribute to or enable antigen binding, e.g., form part or all of the antigen binding site, or can contribute to the inhibition or reduction in function of the antigen or can contribute to the prevention of the antigen interacting with its natural ligands. Fragments thus comprise a heavy chain variable region ($V_H$ domain) and/or a light chain variable region ($V_L$ domain) of the antibodies of the invention. Fragments may also comprise one or more of the heavy chain complementarity determining regions (CDRs) of the antibodies or of the $V_H$ domains, or one or more of the light chain complementarity determining regions (CDRs) of the antibodies, or of the $V_L$ domains.

The term "complementarity determining regions" or "CDRs," as used herein, refers to part of the variable chains in immunoglobulins (antibodies) and T cell receptors, generated by B-cells and T-cells respectively, where these molecules bind to their specific antigen. As the most variable parts of the molecules, CDRs are crucial to the diversity of antigen specificities generated by lymphocytes. There are three CDRs (CDR1, CDR2 and CDR3), arranged non-consecutively, on the amino acid sequence of a variable domain of an antigen receptor. Since the antigen receptors are typically composed of two variable domains (on two different polypeptide chains, heavy and light chain), there are six CDRs for each antigen receptor that can collectively come into contact with the antigen. A single antibody molecule has two antigen receptors and therefore contains twelve CDRs. Sixty CDRs can be found on a pentameric IgM molecule.

Within the variable domain, CDR1 and CDR2 may be found in the variable (V) region of a polypeptide chain, and CDR3 includes some of V, all of diversity (D, heavy chains only) and joining (J) regions. Since most sequence variation associated with immunoglobulins and T cell receptors is found in the CDRs, these regions are sometimes referred to as hypervariable regions. Among these, CDR3 shows the greatest variability as it is encoded by a recombination of the VJ in the case of a light chain region and VDJ in the case of heavy chain regions. The tertiary structure of an antibody is important to analyze and design new antibodies.

Figure 8A:
FIG. 8A is a table showing the protein sequence of scFv H7 heavy chain protein and the protein sequences of CDR-H1, CDR-H2 and CDR-H3 within the scFv H7 heavy chain protein.
Figure 8B:
FIG. 8B is a table showing the protein sequence of scFv H7 light chain protein and the protein sequences of CDR-L1, CDR-L2 and CDR-L3 within the scFv H7 light chain protein.

The term "CDRH1," as used herein, refers to the first CDR region in an antibody heavy chain. The term "CDRH2," as used herein, refers to the second CDR region in an antibody heavy chain. FIG. 8 shows the protein sequence of scFv H7 heavy chain protein and the protein sequences of CDR-H1, CDR-H2 and CDR-H3 within the scFv H7 heavy chain protein.

The term "pH-sensitive antibody" or "pH-dependent antibody," as used herein, refers to an antibody which has a different binding affinity for a target antigen at a first pH than it does for that target antigen at a different pH. As a non-limiting example, an anti-TfR antibody of the invention may be selected for or engineered to have pH-sensitive binding to TfR such that it binds with desirably higher affinity (as described herein) to cell surface TfR at physiological pH 7.4, but upon internalization into an endosomal compartment, rapidly dissociates from TfR at the relatively lower pH (pH 5.5-6.0). Such dissociation may protect the antibody from antigen-mediated clearance and increase the amount of antibody that is either internalized into the target cell or transported across the target cell in the case of a barrier forming cell type. In either case, the effective concentration of the antibody is increased relative to an anti-TfR antibody that does not comprise such pH sensitivity (see, e.g., Chaparro-Riggers et al. J. Biol. Chem. 287(14): 11090-11097; Igawa et al., Nature Biotechnol. 28(11): 1203-1208).

The desired combination of affinities at the serum pH and the endosomal compartment pH can be readily determined for a TfR and conjugated compound by one of ordinary skill in the art.

The term "transferrin receptor" or "TfR," as used herein, refers to a carrier protein for transferrin. TfR may be needed for the import of iron into the cell and is regulated in response to intracellular iron concentration. TfR may import iron by internalizing the transferrin-iron complex through receptor-mediated endocytosis. The existence of a receptor for transferrin iron uptake had been recognized over half a century back. Earlier two transferrin receptors in humans, transferrin receptor 1 and transferrin receptor 2 had been characterized and till recently cellular iron uptake was believed to occur chiefly via these two well documented transferrin receptors. Both these receptors are transmembrane glycoproteins.

TfR1 is a high affinity ubiquitously expressed receptor. Expression of TfR2 is restricted to certain cell types and is unaffected by intracellular iron concentrations. TfR2 binds to transferrin with a 25-30 fold lower affinity than TfR1. Although TfR1 mediated iron uptake is the major pathway for iron acquisition by most cells and especially developing erythrocytes, several studies have indicated that the uptake mechanism varies depending upon the cell type. It is also reported that Tf uptake, independent of these TfRs exists although the mechanisms are not well characterized. The multifunctional glycolytic enzyme Glyceraldehyde 3-phosphate dehydrogenase (GAPDH, EC 1.2.1.12) has been shown to utilize post translational modifications to exhibit higher order moonlighting behavior wherein it switches its function as a holo or apo transferrin receptor leading to either iron delivery or iron export respectively.

The term "endocytosis," as used herein, refers to a form of active transport in which a cell transports molecules (such as proteins) into the cell (endo-+cytosis) by engulfing the molecules in an energy-using process. Endocytosis and its counterpart, exocytosis, are used by all cells because most chemical substances important to them are large polar molecules that cannot pass through the hydrophobic plasma or cell membrane by passive means. Endocytosis may include pinocytosis (cell drinking) and phagocytosis (cell eating).

The term "yeast display" or "yeast surface display," as used herein refers to a technique used in the field of protein engineering. A protein of interest may be displayed as a fusion to the Aga2p protein on the surface of yeast. The Aga2p protein is naturally used by yeast to mediate cell-cell contacts during yeast cell mating. As such, display of a protein via Aga2p projects the protein away from the cell surface, minimizing potential interactions with other molecules on the yeast cell wall. The use of magnetic separation and flow cytometry in conjunction with a yeast display library is a highly effective method to isolate high affinity protein ligands against nearly any receptor through directed evolution.

The term "single-chain variable fragment" or "scFv," as used herein, refers to a fusion protein of the variable regions of the heavy ($V_H$) and light chains ($V_L$) of immunoglobulins, connected with a short linker peptide of ten to about 25 amino acids. The linker may usually be rich in glycine for flexibility, as well as serine or threonine for solubility, and can either connect the N-terminus of the $V_H$ with the C-terminus of the $V_L$, or vice versa. This protein may retain the specificity of the original immunoglobulin, despite removal of the constant regions and the introduction of the linker. scFvs may often be produced in bacteria cell cultures such as E. coli.

ScFvs may be created to facilitate phage display, where it is highly convenient to express the antigen-binding domain as a single peptide. As an alternative, scFv can be created directly from subcloned heavy and light chains derived from a hybridoma. ScFvs have many uses, e.g., flow cytometry, immunohistochemistry, and as antigen-binding domains of artificial T cell receptors. In one embodiment, the present invention discloses scFvs as examples of pH-dependent antibodies. Specifically, Applicants manipulated cellular transport of single-chain antibodies (scFvs) against the transferrin receptor (TfR) by engineering pH-dependent antigen binding. Applicants envision that the methods disclosed herein would be applicable to produce any other pH-dependent antibodies.

The term "saturation mutagenesis," as used herein, refers to a form of random mutagenesis, in which one tries to generate all possible (or as close to as possible) mutations at a specific site, or narrow region of a gene. This is a common technique used in directed evolution. In one embodiment, the present invention relates to methods of histidine saturation mutagenesis for producing pH-dependent antibodies.

As used herein, the terms "proteins" and "polypeptides" are used interchangeably herein to designate a series of amino acid residues connected to the other by peptide bonds between the alpha-amino and carboxy groups of adjacent residues. The terms "protein", and "polypeptide" refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "therapeutic agent" refers to any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The Present Invention

In one aspect, the present invention is a pH-dependent antibody that binds an antigen with higher affinity at a first pH than at a second pH. In one embodiment, the pH-dependent antibody may target and deliver a compound (e.g., a therapeutic agent) into and across cells, such as cancer cells or a blood-brain barrier (BBB). We refer to this improved delivery as "enhanced delivery." In a preferred version of the present invention, the therapeutic agent is delivered to the interior of a cell or across a blood brain barrier at least 2 fold and most preferably at least 2.6 fold more effectively than when compared to delivery without the antibody of the present invention. In one specific embodiment, the association at the second pH/the first pH may be less than 20%.

In one embodiment, the antibody binds at a high affinity, typically in the 1-10 nanomolar range, at the first pH. In other embodiments, the antibody binds with low affinity at the first pH. By "rapid release or "rapid dissociation," we mean that at least 60% (preferably 70%, 80% or 90%) of the antibody dissociates within 10 minutes at the second pH.

In one embodiment, the pH-dependent antibody of the present invention may target a carrier protein. As used herein, the term "carrier protein," refers to a protein that facilitates the diffusion of different molecules, e.g., ions, small molecules, or macromolecules, such as another protein, across a biological membrane. Carrier proteins may be integral/intrinsic membrane proteins; that is, they exist within and span the membrane across which they transport substances. The carrier proteins may assist in the movement of substances by facilitated diffusion or active transport. Each carrier protein may be designed to recognize only one substance or one group of very similar substances. In one specific embodiment, the target protein is a transferrin receptor (TfR).

In one embodiment, the first pH may be any pH value that is different from the second pH. In one embodiment, the first pH may be a physiological pH. In one embodiment, physiological pH is about 7.4 or 7.365.

In one embodiment, the second pH may be any pH value that is different from the first pH. In one embodiment, the second pH may be an endosomal pH. In one embodiment, the second pH may be an endosomal pH within a living cell. In one embodiment, the second pH is within the range of 3-6.5, preferably 4-6, more preferably 4.5-5.8. In one specific embodiment, the second pH is 5.5.

In one embodiment, the pH-dependent antibody comprises at least two consecutive histidine residues at a single complementarity determining region (CDR). In one embodiment, the pH-dependent antibody comprises at least two consecutive histidine residues in an antibody heavy chain. In one embodiment, the pH-dependent antibody comprises at least two consecutive histidine residues in CDRH1.

In one embodiment, the pH-dependent antibody comprises at least three consecutive histidine residues at a single complementarity determining region (CDR). In one embodiment, the pH-dependent antibody comprises at least three consecutive histidine residues in an antibody heavy chain. In one embodiment, the pH-dependent antibody comprises at least three consecutive histidine residues in CDRH1.

In one embodiment, the pH-dependent antibody of the present invention comprises at least 20% histidine residues within an antibody heavy chain, e.g., CDRH1. In one embodiment, the pH-dependent antibody of the present invention comprises at least 30%, preferably 40%, more preferably 50% histidine residues within an antibody heavy chain, e.g., CDRH1.

In one embodiment, the pH-dependent antibody of the present invention may be a mutation of a wild type antibody. While the wild type antibody has 10% or less histidine residues within an antibody heavy chain, the pH-dependent antibody of the present invention comprises at least 10% or more histidine residues than the corresponding wild type one.

In one embodiment, the pH-dependent antibody of the present invention comprises an antibody fragment having an amino acid sequence selected from the group consisting of SEQ ID NOs: 13-20 (corresponding to M4, M8, M10, M11, M16, M17, M20 and M23).

In one embodiment, the pH-dependent antibody of the present invention comprises an antibody fragment having an amino acid sequence of RLNYNSHHMH (SEQ ID NO:13).

In one embodiment, the pH-dependent antibody of the present invention comprises an antibody fragment having an amino acid sequence of HYNYSNYPMH (SEQ ID NO:14).

In one embodiment, the pH-dependent antibody of the present invention comprises an antibody fragment having an amino acid sequence of HLHHNHHPLH (SEQ ID NO:15).

In one embodiment, the pH-dependent antibody of the present invention comprises an antibody fragment having an amino acid sequence of RLNFHHHAMH (SEQ ID NO:16).

In one embodiment, the pH-dependent antibody of the present invention comprises an antibody fragment having an amino acid sequence of RYPFHHHDHH (SEQ ID NO:17).

In one embodiment, the pH-dependent antibody of the present invention comprises an antibody fragment having an amino acid sequence of RFHHHRYAQH (SEQ ID NO:18).

In one embodiment, the pH-dependent antibody of the present invention comprises an antibody fragment having an amino acid sequence of RFPFHHHPIH (SEQ ID NO:19).

In one embodiment, the pH-dependent antibody of the present invention comprises an antibody fragment having an amino acid sequence of RFSFHHHPIH (SEQ ID NO:20).

In one preferred embodiment, the pH-dependent antibody of the present invention comprises an antibody fragment having an amino acid sequence of RYPFHHHDHH (SEQ ID NO:17).

In one embodiment, pH-dependent antibody of the present invention is an isolated antibody fragment having the amino acid sequence set forth in any one of SEQ ID NOs. 13-20. In some preferred versions, the isolated antibody fragment is a single chain fragment variable (scFv) fragment.

In some embodiments, the invention provides pH-dependent antibodies that bind carrier proteins or endothelial cell receptors resulting in endocytosis of the proteins or receptor and bound ligands. In some embodiments, the invention is a pharmaceutical composition comprising a pH-dependent antibody linked to a pharmaceutically active compound that is useful in transferring the pharmaceutically active compound across the blood brain barrier (BBB).

Table 1 in the Example shows the exemplary pH-dependent antibodies according to one embodiment of the present invention.

In one aspect, the present invention is an antibody-targeted brain delivery system comprising a pH-dependent antibody as discussed above.

In one embodiment, the pH-dependent antibody may be used to deliver a therapeutic agent into a cell (e.g., a cancer cell) or a BBB system. Taking a BBB system as an example, a variety of brain drug cargoes, e.g. pharmacologic compounds or, equivalently, pharmaceutically active compounds, may be delivered successfully in vivo by using the pH-dependent antibody-based targeting according to the invention and are "therapeutic agents" of the present invention. As used herein, the terms "pharmaceutically active compound" and "pharmacologic compound" shall refer to any compound useful in treating or ameliorating the effects of a disease or disorder. For example, diseases including neurodegenerative diseases such as Alzheimer's disease, Parkinson's disease, Huntington's disease, amyotrophic lateral sclerosis (ALS, Lou Gehrig's disease) and multiple sclerosis can be targeted by use of such drugs as neurotrophic factors, including, but not limited to, nerve growth factor (NGF), brain derived neurotrophic factor (BDNF), ciliary neurotrophic factor (CNTF), glial cell-line neurotrophic factor (GDNF) and insulin-like growth factor (IGF).

In addition, other compounds that have been shown to have therapeutic potential and may be delivered by antibodies of the invention are neuropeptides, including, but not limited to, Substance P, neuropeptideY, vasoactive intestinal peptide (VIP), gamma-amino-butyric acid (GABA), dopamine, cholecystokinin (CCK), endorphins, enkephalins and thyrotropin releasing hormone (TRH). Further, therapeutics may include cytokines, anxiolytic agents, anticonvulsants, polynucleotides and transgenes, including, for example, small interfering RNAs which may be used for such neuronal disorders, including, but not limited to, psychiatric illnesses, such as, for example anxiety, depression, schizophrenia, and sleep disorders, as well as epilepsies, seizure disorders, stroke and cerebrovascular disorders, encephalitis and meningitis, memory and cognition disorders, pain therapeutics and physical trauma.

In one aspect, the present invention are formulations for delivering a molecule (e.g., a therapeutic agent) through BBBs or into cells (e.g., cancer cells).

In one configuration, the present formulations may include pH-dependent antibodies as disclosed herein as the enhancing agent for a molecule (e.g., a therapeutic agent.) In one embodiment of this configuration, the present formulations may be free of any other active compounds. The active compounds may be added after the formulation is administered to a subject. In other embodiments of this configuration, the present formulations may also include active compounds or therapeutic agents other than pH-dependent antibodies. As such, the active compounds or therapeutic agent are administered to a subject at the same time as the administration of the pH-dependent antibodies.

The formulation of the present invention may also include other suitable agents such as carriers or vehicles. As used herein, the term "carrier" refers to a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials.

In one aspect, the present invention is a method of delivering a therapeutic agent or molecule through a blood-brain barrier (BBB) of a subject. In one embodiment, the method comprises the steps of (a) obtaining a pH-dependent antibody according to any embodiment as discussed above; (b) exposing the BBB of the subject to a pharmaceutically effective amount of the pH-dependent antibody; and (c) exposing the BBB of the subject to a pharmaceutically effective amount of the therapeutic agent or molecule, wherein the therapeutic agent or molecule is delivered though the BBB in an enhanced manner. In another aspect, the present invention is a method of delivering a therapeutic agent into a cell, preferably a cancer cell. In one embodiment, the method comprises the steps of (a) obtaining a pH-dependent antibody according to any embodiment as discussed above; (b) exposing cancer cell to a pharmaceutically effective amount of the pH-dependent antibody; and (c) exposing a cancer cell to a pharmaceutically effective amount of the therapeutic agent, wherein the therapeutic agent is delivered to the interior of the cancer cell in an enhanced manner.

In a preferred embodiment, the delivery described above is in vivo and is part of a treatment regime for a patient. This delivery would typically be similar to the manner in which other therapeutic antibodies are delivered to patients. For example, any cancer-targeted immunotoxin would be exemplary. One would use the pH sensitive antibody of the present invention as a targeting and internalizing antibody to enhance intracellular uptake. One may examine the following references for examples of appropriate delivery strategies: (1) Du X, Beers R, Fitzgerald D J, Pastan I (2008) Differential cellular internalization of anti-CD19 and -CD22 immunotoxins results in different cytotoxic activity. *Cancer Res* 68(15):6300-6305. (2) Klussman K, et al. (2004) Secondary mAb-vcMMAE conjugates are highly sensitive reporters of antibody internalization via the lysosome pathway. *Bioconjug Chem* 15(4):765-773. (3) Sutherland M S, et al. (2006) Lysosomal trafficking and cysteine protease metabolism confer target-specific cytotoxicity by peptide-linked anti-CD30-auristatin conjugates. *J Biol Chem* 281 (15):10540-10547. (4) Weldon J E, et al. (2009) A protease-resistant immunotoxin against CD22 with greatly increased activity against CLL and diminished animal toxicity. *Blood* 113(16):3792-3800.

In one embodiment, the molecule to be delivered may be any compound or substance as appreciated by one skilled in the art. In one embodiment, the molecule may be a compound or substance that has large molecular weight. For example, in one embodiment, the molecule to be delivered may have a molecular weight larger than 500 Da.

In one embodiment, any of the pH-dependent antibodies as disclosed herein may be used in the method of the present invention. The Example shows methods for producing the pH-dependent antibodies.

Applicants envision that proteins could be adapted to function in a range of subcellular pH environments through non-random placement of histidine residues. By using single-chain antibodies (scFvs) as an example, Applicants demonstrated that engineering pH-dependent antigen binding of scFvs can lead to manipulation of cellular transport of the scFvs against the corresponding carrier protein, i.e., transferrin receptor (TfR).

In some embodiments, the pH-dependent antibodies may be produced from mutation of the corresponding wild type antibodies. Applicants envision that any method of mutations as appreciated by one skilled in the art may be used in the present invention.

In one embodiment, the present method uses saturation mutagenesis, for example, histidine saturation mutagenesis, to obtain a suitable antibody.

In one specific embodiment, a wild type antibody, e.g., an anti-TfR scFv, may be subjected to histidine saturation mutagenesis of a single CDR. By employing yeast surface display with a pH-dependent screening pressure, the antibody, e.g., scFvs, having markedly increased dissociation from TfR at endosomal pH (e.g., pH 5.5) may be identified. In one specific embodiment, the pH-sensitivity may generally result from a central cluster of histidine residues in an antibody heavy chain (e.g., CDRH1). The Example shows an exemplary method of obtaining or producing pH-dependent antibodies.

After the pH-dependent antibody is obtained, a subject's BBB or cancer cells may be exposed to a pharmaceutically effective amount of the pH-dependent antibody. Applicants show that the pH-dependent antibodies exhibited rapid dissociation at endosomal pH, while maintaining a high affinity for TfR at neutral pH. After treatment with pH-dependent antibodies, it is easier for the molecule to be delivered to pass through the BBB of the subject or through cancer cell membranes.

The BBB of the subject or cancer cells may be further exposed to a pharmaceutically effective amount of the molecule, wherein the molecule is delivered though the BBB.

In one embodiment, the BBB of the subject or cancer cells may be exposed to the molecule after the BBB is exposed to the pH-dependent antibody.

In one embodiment, the BBB of the subject or cancer cells may be exposed to the molecule at the same time as the BBB being exposed to the pH-dependent antibody.

In one embodiment, the therapeutic agent to be delivered is linked to the pH-dependent antibody. For example, the agent may be covalently or non-covalently attached or may be part of a fusion protein. By "linked," we mean to include all manner of associating the therapeutic agent with the antibody so that both can be delivered at the same time.

In general, methods of conjugating, linking and coupling antibodies to pharmacologically active compounds are well known in the field. For example, see, Wu A M, Senter P D, Arming antibodies: prospects and challenges for immunoconjugates, *Nat Biotechnol.* 2005 September; 23(9):1137-46 and Trail P A, King H D, Dubowchik G M, Monoclonal antibody drug immunoconjugates for targeted treatment of cancer, *Cancer Immunol Immunother.* 2003 May; 52(5):328-37; Saito G, Swanson J A, Lee K D. Drug delivery strategy utilizing conjugation via reversible disulfide linkages: role and site of cellular reducing activities, *Adv Drug Deliv Rev.* 2003 Feb. 10; 55(2):199-215. One may wish to use non-covalent linkage of the proposed antibody to pharmacologically active component. For example, one could use biotin/streptavidin interaction, such as the disclosure taken from Jones, A. R. and E. V. Shusta, Blood-brain barrier transport of therapeutics via receptor-mediation. *Pharmaceutical Research,* 2007. 24(9): p. 1759-1771.

In one embodiment, the target cell or BBB may be exposed to a pharmaceutically effective amount of the pH-dependent antibody at a pH different from the neutral pH. In one embodiment, the pH at which the target may be exposed to a pharmaceutically effective amount of the pH-dependent antibody is an endosomal pH, e.g., 3-6, preferably 4-5.8, more preferably 5.5.

In one aspect, the present invention is a vector comprising a pH-dependent antibody as discussed herein or a microorganism comprising the vector.

In another exemplary embodiment, the invention is an expression vector that includes a polynucleotide encoding the amino acid sequence set forth in any one of SEQ ID NOs. 13-20. In other embodiments, the invention includes a purified and isolated host cell comprising the expression vector containing the isolated nucleic acid encoding the amino acid sequence set forth in any one of SEQ ID NOs. 13-20. It should be appreciated that the host cell can be any cell capable of expressing antibodies, such as, for example microbacteria such as *E. coli*; fungi; mammalian cells, including the Chinese hamster ovary cells; insect cells, using, for example, a baculovirus expression system; plant cells, such as, for example, corn, rice, *Arabidopsis*, and the like. See, generally, Verma, R. et al., *J Immunol Methods.* 1998 Jul. 1; 216(1-2):165-81.

In some versions of this embodiment, the microorganism is selected from the group consisting of: yeast, bacteria, and combinations thereof. In some preferred embodiments the host cell is *Saccharomyces cerevisiae* or *E. coli*.

As well, the BBB-targeting antibodies or cancer cell-targeting antibodies may be provided in combination with liposome, nanoparticles or other analogous carriers loaded with a pharmaceutically active compound. Methods of preparing such compositions are known in the field (see, for example, Sugano et al., Antibody Targeting of Doxorubicin-loaded Liposomes Suppresses the Growth and Metastatic Spread of Established Human Lung Tumor Xenografts in Severe Combined Immunodeficient Mice, *Cancer Research* 60, 6942-6949, Dec. 15, 2000 and Martin et al., Nanomaterials in Analytical Chemistry, *Analytical Chemistry News & Features,* May 1, 1998; pp. 322 A-327 A). As used herein, the phrase "antibody in combination with a pharmaceutically active compound" shall not be limited by the method of manufacture and such compositions may be produced by, but not limited to, techniques of conjugating, linking, coupling and decorating known in the art.

Applicants envision that certain residues (e.g., Lysine) of either the targeting vector or the protein therapeutic would be biotinylated using one of a number of commercial methods (such as N-hydroxysuccinimide biotin analogs). Then, either the vector or the therapeutic (whichever one was not modified in the previous step) would be conjugated to streptavidin or one of its variants (e.g., neutravidin) using one of the other methods presented here. The monobiotinylated reagent and the streptavidin conjugated counterpart would be combined and the near-covalent binding affinity would keep the reagents together.

One may wish to express the pH-dependent antibody as a fusion protein with a pharmacologically or therapeutically relevant peptide. For example, one may wish to express a scFv of the present invention with a protein linker and a protein therapeutic. Standard molecular biology techniques (e.g., restriction enzyme based subcloning, or homology based subcloning) could be used to place the DNA sequence encoding a protein therapeutic in frame with the targeting vector (usually a protein linker is also added to avoid steric hindrance). The fusion protein is then produced as one peptide in a host cell (e.g., yeast, bacteria, insect, or mammalian cell) and purified before use. Note the therapeutic does not need to be a whole protein. (For example, it can be a single peptide chain as a subunit in a protein with more than one peptide. The other peptides can be co-expressed with the vector fusion and allowed to associate in the host cell or after secretion).

Applicants envision that one may also include large particles as "therapeutic" compounds. For example, one may wish to decorate liposomes or nanoparticles with an embodiment of the targeting vector. Preferably, procedures to create vector-decorated liposomes may be taken from Jones, A. R. and E. V. Shusta, Blood-brain barrier transport of therapeutics via receptor-mediation. *Pharmaceutical Research,* 2007. 24(9): p. 1759-1771. Liposomes may be created using phospholipids, one of which is poly-ethylene glycol-distearoylphosphatidylethanolamine (PEG-DSPE) functionalized with maleimide as in the chemical linkage described above. The liposomes can be created such that they encapsulate a therapeutic in the lipid-based sphere. The vector may be modified using Traut's reagent and attached to the surface of the liposome as described in the chemical linkage methods. Note: Nanoparticles can be treated in the same way, except that the particles are solid-based (e.g., polybutylcyanoacrylate) and must be artificially PEGylated before reaction with modified vectors.

In some embodiments of the present invention, pH-dependent antibodies may be administered with or without above modifications. One may wish to administer the pH-dependent antibodies of the present invention without the modifications described above. For example, one may administer the antibodies through an intravenous injection or through intra-peritoneal and subcutaneous methods.

In one aspect, the present invention is a kit for delivering a therapeutic agent through a blood-brain barrier (BBB) or a cell (e.g., cancer cell) of a subject. In one embodiment, the kit comprises a pH-dependent antibody according to any embodiment as discussed herein, possibly already linked to a therapeutic agent or with means to link to a therapeutic agent.

In one embodiment, the kit of the present invention may include a therapeutic device for delivering the pH-dependent antibodies and/or an active compound. In one embodiment, the therapeutic device may be any suitable devices charged with a preparation of the pH-dependent antibodies. In another embodiment, the therapeutic device may comprise any suitable devices charged with a preparation of the pH-dependent antibodies and/or an active compound and at least one additional active compound.

The instant invention may also include kits, packages and multicontainer units containing the above described pharmaceutical compositions, active ingredients, and/or means for administering the same for use in the prevention and treatment of diseases and other conditions in mammalian subjects. Briefly, these kits include a container or formulation that contains the pH-dependent antibodies, and/or other biologically active agents, possibly in combination with delivery enhancing agents disclosed herein formulated in a pharmaceutical preparation for delivery.

EXAMPLES

Various exemplary embodiments of compounds obtained as generally described above and methods according to this invention will be understood more readily by reference to the following examples, which are provided by way of illustration and are not intended to be limiting of the invention in any fashion.

The equilibrium binding affinity of receptor-ligand or antibody-antigen pairs may be modulated by protonation of histidine side-chains, and such pH-dependent mechanisms play important roles in biological systems, affecting molecular uptake and trafficking. Here, we aimed to manipulate cellular transport of single-chain antibodies (scFvs) against the transferrin receptor (TfR) by engineering pH-dependent antigen binding. An anti-TfR scFv was subjected to histidine saturation mutagenesis of a single CDR. By employing yeast surface display with a pH-dependent screening pressure, scFvs having markedly increased dissociation from TfR at pH 5.5 were identified. The pH-sensitivity generally resulted from a central cluster of histidine residues in CDRH1. When soluble, pH-sensitive, scFv clone M16 was dosed onto live cells, the internalized fraction was 2.6-fold greater than scFvs that lacked pH-sensitive binding and the increase was dependent on endosomal acidification. Differences in the intracellular distribution of M16 were also observed consistent with an intracellular decoupling of the scFv M16-TfR complex. Engineered pH-sensitive TfR binding could prove important for increasing the effectiveness of TfR-targeted antibodies seeking to exploit endocytosis or transcytosis for drug delivery purposes.

Here we reasoned that the intracellular accumulation of an anti-TfR antibody could be increased by engineering enhanced dissociation from TfR at endosomal pH, thereby decoupling antibody uptake from post-internalization TfR trafficking dynamics. To test this hypothesis, an anti-TfR single-chain antibody (scFv) was subjected to histidine-saturation mutagenesis at a single CDR known to participate in TfR binding, and the resultant library was screened. These methods resulted in an scFv, M16, that exhibited rapid dissociation at endosomal pH, while maintaining a high affinity for TfR at neutral pH. When dosed onto proliferating cancer cells, M16 displayed greater total cellular association than the wild-89 type scFv H7, which could be attributed to elevated intracellular accumulation. Immunocytochemical analysis revealed markedly different patterns of accumulation for scFv M16, indicating a departure in trafficking from the canonical Tf-TfR pathway.

Materials and Methods

Cells, Media, and Plasmids

SK-BR-3 cells (HTB-30) were obtained from American Type Culture Collection (ATCC) and maintained at 37° C., 5% CO2, in growth medium (SKBR3GM) composed of McCoy's 5A basal media (10050CV, Corning-Cellgro) supplemented with 10% fetal bovine serum (Gibco) and 1× antibiotic/antimycotic solution (PSA, Gibco). *Saccharomyces cerevisiae* strains EBY100 [26] and AWY100 [27] were used for surface display, while strain YVH10 [28] was used for soluble scFv secretion. The vector pCT-ESO [29] was the backbone for all scFv surface-display experiments, while plasmid pRS316-GAL-4420 [30] provided the backbone for scFv secretion. EBY100 were grown in SD-CAA (20 g/L dextrose, 6.7 g/L yeast nitrogenous base, 100 mM sodium phosphate buffer pH 6.0, 5.0 g/L bacto-casamino acids lacking tryptophan and uracil). AWY100 was grown in SD-CAA supplemented with 40 mg/L uracil. YVH10 were grown in SD-2×SCAA+Trp (20 g/L dextrose, 6.7 g/L yeast nitrogenous base, 100 mM sodium phosphate buffer pH 6.0, 190 mg/L Arg, 108 mg/L Met, 52 mg/L Tyr, 290 mg/L Ile, 440 mg/L Val, 220 mg/L Thr, 130 mg/L Gly, 40 mg/L Trp, lacking leucine and uracil). Induction medium (SG-CAA or SG-2×SCAA) was composed of SD-CAA or SD-2×SCAA with 20 g/L D-galactose instead of dextrose. Solid media for individual colony selection were made identically to the above yeast media recipes with the addition of 15 g/L bacto-agar and 180 g/L d-sorbitol. During FACS, sorted EBY100 were collected into SD-CAA supplemented with 50 mg/L kanamycin sulfate (K4378, Sigma-Aldrich) to prevent bacterial growth.

Histidine-Saturation Mutagenesis of scFv H7 CDRH1 and Library Construction

The scFv H7 against human transferrin receptor was a kind gift from Dr. James Marks at the University of California-San Francisco [31]. The negative control for surface display and soluble scFv assays was an anti-hen egg lysozyme antibody, scFv D1.3 [32]. scFv H7 was previously subcloned into the pCT-ESO backbone to create the plasmid 118 pESO-H7 [33]. pESO H7 formed the basis for constructing a recombinant, histidine-saturation library focused on scFv H7 CDRH1. To allow homologous recombination (and to preemptively silence any yeast receiving reclosed vector during the transformation), site-directed mutagenesis was used to create a unique restriction enzyme site (SpeI) followed by a double stop codon in the middle of CDRH1. Briefly, Phusion DNA polymerase (NEB) was used to linearly amplify and mutate the pESO-H7 template with primers H7sdmF 5'-GCCTCTCGATTCACCTTCACTAGT-TAATAAATGCACTGGGTCCGC-3' (SEQ ID NO:29) and H7sdmR 5'-CTGGCGGACCCAGTGCATTTAT-TAACTAGTGAAGGTGAATCGAGAGGCCAG-3' (SEQ ID NO:30). The resulting PCR product was digested with DpnI (NEB), ethanol precipitated in the presence of sodium acetate and pellet paint (Covagen), rehydrated in 1× TE, and digested with DpnI a second time. After successful transformation into XL1 Blue Supercompetent cells (Agilent) following the manufacturer's protocol, plasmid DNA was rescued from individual colonies using the Zyppy kit (Zymo Research), and introduction of the desired mutations comprising pESO132 H7sdm (FIG. 1A) was verified with bi-directional sequencing using the primers BTSeqF 5'-CTGCTCCGAACAATAAAGATTCTAC-3' (SEQ ID NO:31) and BTSeqR 5'-GTATGTGTAAAGTTGGTAACGGAAC-3'(SEQ ID NO:32).

FIGS. 1(A and B) shows creation and screening methodology for a histidine-saturated CDRH1 library based on the wild-type anti-TfR scFv, H7. As shown in FIG. 1A, the pESO-H7sdm vector contained the coding sequence for wild-type scFv H7, harboring a unique restriction site (SpeI) followed by two stop codons in CDRH1. SpeI digestion of pESO-H7sdm produced a linearized backbone that would be undetectable by flow cytometry if introduced as a reclosed vector into yeast. A double-stranded DNA cassette containing the histidine-saturated CDRH1 was built using two cycles of PCR, from primers and a degenerate oligonucleotide (IP90T). Although depicted as a single entity for simplicity, IP90T was in fact a mixture of millions of unique 143 ssDNA oligos representing all possible combinations of histidine in CDRH1. The CDRH1his cassette and linearized pESO-H7sdm were used to create the CDRH1his library by homologous recombination in yeast.

As shown in FIG. 1B, screening and assessment of yeast-displayed scFvs was accomplished by saturating with recombinant human transferrin receptor (rhTfR) followed by a 10 minute incubation in acidic buffer (pH 4.0-6.5) and assay for TfR dissociation. A pH 5.5 buffer was used to simulate endosomal conditions relevant to transferrin-TfR dissociation [19, 20]. A dissociation control was included by using a pH 7.4 buffer as opposed to acidic buffer at this step. The dissociation process was halted by addition of an excess volume of ice cold pH 7.4 buffer. Surface constructs were subsequently immunolabeled and analyzed by flow cytometry. The histogram depicts the response of yeast-displayed wild-type scFv H7 to 10 minute incubation with buffers having acidic pH.

Next, a DNA cassette containing the histidine-saturated CDRH1 was fabricated from a 90 bp oligonucleotide mix and two complementary oligonucleotide primers. The 90 bp mixed oligonucleotide DNA (purchased from IDT) was designed using degenerate bases, allowing the possibility of histidine at every codon in CDRH1, while maintaining 30 bp homology to wild-type scFv H7 at both the 5' and 3' ends (IP90T 5'-AGGTCCCTGAGACTCTCCTGTGCAGC-CTCTCRWYWCMMCYWCMRTMRCYATSMTMWK-CACTGGGTCCGCCAGGCTCCAGGCAAGGGGCTG-3' (SEQ ID NO:33), where S=G/C, R=A/G, Y=C/T, K=G/T, M=A/C, W=A/T). IP90T was made double-stranded and extended to 100 bp via 5 cycles of standard PCR with OneTaq 2× GC Master Mix (NEB) and a single primer IPCDH1ampF 5'-CCACCCACTCCAGCCCCTTGCCTG-GAGC-3' (SEQ ID NO:34) (FIG. 1a). The size and homogeneity of the product were verified by agarose gel electrophoresis. A DNA Clean and Concentrate 5 kit (Zymo Research) was used to purify the 100 bp PCR product. The final mutagenic DNA cassette was produced by a second PCR reaction with OneTaq 168 2× GC Master Mix using the first PCR product as a template and the primers IPCDH1ampF and IPCDH1ampR 5'-CCAGCCTGGGAG-GTCCCTGAGACTCTCCTGTGC-3'(SEQ ID NO:35). The resulting 120 bp double-stranded cassette was separated by agarose gel electrophoresis and purified with the Zymoclean kit (Zymo Research).

Finally, the H7CDRH1his library was created by electroporation and homologous recombination of the histidine-saturated 120 bp mutagenic DNA cassette, and the (SpeI) linearized pESO-H7sdm acceptor vector in yeast [34, 35] (FIG. 1A). Library size was determined by plating serial dilutions and colony counting. A dozen yeast colonies were selected at random and plasmid DNA was rescued with the Zymoprep II kit (Zymo Research). The type (histidine or non-histidine) and distribution of mutations in the scFv H7 were ascertained by sequencing as described above. All mutations were found confined to the CDRH1 (Table 1).

TABLE 1

CDRH1 amino acid sequences of CDRH1his clone subsets scFv H7 wild type CDRH1[a]

| | | R | F | T | F | S | S | Y | A | M | H |
|---|---|---|---|---|---|---|---|---|---|---|---|
| | | 28 | 29 | 30 | 31 | 32 | 33 | 34 | 35 | 36 | 37 |

Randomly selected clones from CDRH1his

| | | R | F | T | F | S | S | Y | A | M | H |
|---|---|---|---|---|---|---|---|---|---|---|---|
| LD1 | SEQ ID NO: 1 | R | F | P | L | S | H | H | D | I | H |
| LD2 | SEQ ID NO: 2 | R | F | H | H | S | R | Y | D | M | H |
| LD3 | SEQ ID NO: 3 | R | Y | T | F | H | R | Y | A | K | H |
| LD4 | SEQ ID NO: 4 | R | Y | N | Y | R | R | Y | D | I | H |
| LD5 | SEQ ID NO: 5 | Q | F | T | Y | N | R | H | P | M | H |
| LD6 | SEQ ID NO: 6 | H | Y | H | L | S | S | Y | H | L | H |
| LD7 | SEQ ID NO: 7 | R | F | N | L | N | H | H | H | H | H |
| LD8 | SEQ ID NO: 8 | H | H | N | H | R | N | Y | A | H | H |
| LD9 | SEQ ID NO: 9 | R | Y | P | F | S | S | Y | H | L | H |
| LD10 | SEQ ID NO: 10 | R | F | T | Y | N | S | Y | A | K | H |
| LD11 | SEQ ID NO: 11 | R | F | T | T | S | H | H | P | H | H |
| LD12 | SEQ ID NO: 12 | R | H | T | F | S | S | Y | A | H | H |

CDRH1 mutants with increased dissociation at pH5.5

| M4 | SEQ ID NO: 13 | R | L | N | Y | N | S | H | H | M | H |
| M8 | SEQ ID NO: 14 | H | Y | N | Y | S | N | Y | P | M | H |
| M10 | SEQ ID NO: 15 | H | L | H | H | N | H | H | P | L | H |
| M11 | SEQ ID NO: 16 | R | L | N | F | H | H | H | A | M | H |
| M16 | SEQ ID NO: 17 | R | Y | P | F | H | H | H | D | H | H |
| M17 | SEQ ID NO: 18 | R | F | H | H | H | R | Y | A | Q | H |
| M20 | SEQ ID NO: 19 | R | F | P | F | H | H | H | P | I | H |
| M23 | SEQ ID NO: 20 | R | F | S | F | H | H | H | P | I | H |

CDRH1 mutants with reduced dissociation at pH5.5

| N4 | SEQ ID NO: 21 | R | F | H | F | N | R | Y | H | M | H |
| N5 | SEQ ID NO: 22 | R | F | T | F | N | N | Y | A | M | H |
| N7 | SEQ ID NO: 23 | R | H | H | L | S | S | Y | D | M | H |
| N10 | SEQ ID NO: 24 | R | F | H | L | N | S | Y | D | M | H |
| 5P4 | SEQ ID NO: 25 | Q | F | H | F | N | N | Y | D | L | H |
| 5P7 | SEQ ID NO: 26 | R | F | T | F | S | H | Y | D | L | H |
| 5P9 | SEQ ID NO: 27 | R | F | T | F | S | N | Y | H | H | H |
| 5P15 | SEQ ID NO: 28 | Q | H | N | L | R | S | Y | H | L | H |

[a]The wild-type H7 CDRH1 is shown across the top with heavy chain residue numbers above (Kabat numbering). Heat maps and percentages at the top of every section indicate the relative incidence of histidine at that position for the clones in the table; darker corresponds to higher incidence. Bold font indicates a mutation from wild-type and bold-underline font indicates histidine.

FACS-Based Screening and Selection of pH-Sensitive scFv

Yeast for surface display were grown in SD-CAA at 30° C., 260 rpm, and overnight. The following day, cultures were diluted to an OD600 nm of 0.3 and grown for ~4 hours until the OD600 nm reached 1.0. Induction of surface display was accomplished by replacing SD-CAA with an equivalent volume of SG-CAA (SD-CAA with 20 g/L D-galactose instead of dextrose) and incubating at 20° C., 260 rpm for 16-20 h. Finally, induced yeast were washed three times in ice-cold 100 mM phosphate buffer containing 50 mM NaCl and 1 g/L bovine serum albumin (PBSA pH 7.4). Unless specifically noted, PBSA was the default buffer used for all washing, dilution, and resuspension steps.

The CDRH1his library contained approximately $3 \times 10^7$ members and was initially enriched for TfR binders at neutral pH to ensure scFv retained wild-type functionality prior to imposing pH 5.5 selection pressure. For the first two rounds of sorting, $1 \times 10^8$ induced yeast cells were incubated with 2 mL 50 nM recombinant human TfR (rhTfR, soluble extracellular domain, R&D systems) to saturate scFv binding. After rotating at room temperature for two hours, yeast were washed twice with PBSA to remove non-specifically bound rhTfR. In parallel, $2 \times 10^6$ control yeast (H7 or D1.3) were incubated in 100 μL of 50 nM rhTfR. After washing, yeast were prepared for FACS; all subsequent washing and immunolabeling steps were carried out at 4° C. to prevent further antigen dissociation. Full-length expression was detected using a rabbit polyclonal antibody against the c-myc epitope tag (PA1-24484, Thermo-Fisher, diluted 1:1000), followed by goat an anti-rabbit Alexa 488-conjugated secondary antibody (A-11008, Life Technologies, diluted 1:500). TfR-binding was detected by a mouse monoclonal anti-hTfR antibody (R&D Systems, clone 29806, diluted 1:100) followed by a goat anti-mouse Alexa647-conjugated secondary antibody (A-21235, Invitrogen, diluted 1:500). Yeast libraries were sorted in purity mode at approximately $1 \times 10^7$ events per hour on a FACSAriaII (Becton-Dickinson).

Following two rounds of enrichment for pH 7.4 binding, two rounds of sorting were carried out that included a pH 5.5 incubation step to isolate pH-sensitive binders. $1 \times 10^7$ induced, washed yeast were incubated with saturating levels of rhTfR, pH 7.4, (0.5 mL of 50 nM rhTfR in PBSA) at room temperature, for 2 h. The yeast were pelleted by centrifugation and the rhTfR solution was aspirated. Yeast were resuspended in 1 mL 200 mM MES buffer (35.71 g/L Sodium MES, 7.57 g/L MES Monohydrate) pH 5.5 containing 1 g/L BSA (MBSA) and rotated at room temperature for 10 min. The reaction was quenched by adding 4 mL ice-cold PBSA (pH7.4) and immediately pelleting the yeast. Two additional washes in ice-cold PBSA were carried out, prior to labeling the yeast for FACS as described above. $2 \times 10^6$ control yeast (H7 and D1.3) were prepared identically both with and without the pH 5.5 shift, to serve as experimental and gating controls.

The pH shift procedure described for screening was adapted for evaluation of individual clones. Pools from the selection process above were plated on SD-CAA at a 1:10,000 dilution. Single colonies were selected, grown, induced and washed as described above. $2 \times 10^6$ washed, induced yeast were incubated, rotating for 2 h. at room temperature with 100 μL of 20 nM rhTfR. The yeast were pelleted by centrifugation and the rhTfR solution was aspirated. Yeast were resuspended in 200 μL of 200 mM MES pH 5.5 containing 1 g/L BSA (MBSA) and rotated at room temperature for 10 min. Alternately, some samples were resuspended in 200 μL PBSA to serve as neutral pH dissociation controls. All reactions were quenched by adding 1 mL ice-cold PBSA and immediately pelleting the yeast. Two additional washes in PBSA were carried out, prior to labeling the yeast for FACS as described above. Geometric mean fluorescence intensities of the antigen binding populations (MFI, background fluorescence from scFvD1.3-displaying yeast subtracted) were quantified with the FlowJo (Tree Star). Fraction rhTfR bound was calculated by dividing the MFI at pH 5.5 by MFI pH7.4.

Apparent Equilibrium Binding Affinity of scFv on Yeast Surface

Serial dilutions of rhTfR ranging from 2 pM-50 nM were prepared in PBSA, at sufficient volume to avoid ligand-depleting conditions. ScFvs M16, N5, H7, and D1.3 were freshly transformed by the LiAc/ssDNA/PEG method [36] into the appropriate yeast strains for surface display. Yeast were grown and induced as above; $5 \times 10^5$ induced yeast displaying a given scFv clone, were collected and washed twice in PBSA. Washed yeast were incubated with rhTfR dilutions, shaking in a 20° C. incubator for 3 h. Expression and TfR binding were analyzed by flow cytometry (FACSCalibur, Becton-Dickinson) using the same primary and secondary antibodies described above, collecting at least 15,000 cell events per sample. Fraction of rhTfR bound (with background due to non-specific binding by negative control scFv D1.3 subtracted), was quantified using fluorescence data (MFI) from the A647 (anti-TfR) channel Fraction bound values were fit to a bimolecular equilibrium binding model to determine the apparent equilibrium binding constant (Kd).

Secretion and Purification of Soluble scFv

Soluble scFv were secreted and purified from YVH10 supernatants as detailed previously [33]. Briefly scFvs were subcloned into the pRS316-GAL-4420 expression vector and transformed into YVH10. After 72 h growth in SD-2× SCAA and 72 h induction in SG-2×SCAA at 20° C., supernatants were collected, sterile-filtered, dialyzed into TRIS-buffered saline (TBS, 25 mM Tris, 150 mM NaCl, 2 mM KCl, pH 7.9) and scFv were purified using Ni-NTA Superflow resin (Qiagen). Purified scFv was dialyzed in Dulbecco's PBS (2.68 mM KCl, 136.89 mM NaCl, 8.10 mM Na2HPO4, 1.47 mM KH2PO4, Sigma-Aldrich), 0.2 uM filtered, and stored at 4° C. ScFv purity was analyzed by SDS-PAGE and Western blotting, while protein concentration was measured using the Bradford Reagent (Sigma-Aldrich). ScFv D1.3, was secreted, purified, and employed as a negative control.

Binding and pH-Sensitive Dissociation of rhTFR from Soluble scFvs

To assay for specific activity of the purified scFv, streptavidin-coated Dynabeads Biotin-Binder™ paramagnetic particles (~2.8 um diameter, Life Technologies) at a concentration of $1 \times 10^7$ particles/mL, were incubated with biotinylated mouse anti-c-myc MAb (clone 9E10, 05-419, EMD Millipore, diluted 1:250) in TRIS-buffered saline containing 1 g/L BSA (TBSA, 100 mM TRIS, 150 mM NaCl, pH 7.4) overnight, at room temperature. 9E10 MAb-coated particles were washed three times in TBSA, divided into aliquots ($1 \times 10^5$ particles each), and dispensed into 96-well polypropylene plates. Subsequently, scFvs were captured on the particles through their carboxy-terminal c-myc epitope. To accomplish scFv capture, 200 μL of purified scFv at a concentration of 100 nM (an amount known to saturate available 9E10 on the bead surface) was added to each experimental well and allowed to equilibrate for 2 h. The particles were washed once with TBSA, resuspended in 50 uL of saturating amounts of rhTfR (50 nM), and equilibrated for 1 h. The particles were collected magnetically and the rhTfR solution was aspirated. Particles were resuspended in 200 μL MBSA, pH 5.5 and incubated at room temperature for 10 min. Alternately, particles were resuspended in 200 μL TBSA, pH 7.4 to serve as neutral pH dissociation controls. All reactions were quenched by adding 300 μL ice cold TBSA and immediately isolating the particles. Fluorescent labeling was completed using ice-cold reagents with the plate resting on ice. Two additional washes in TBSA were carried out, prior to labeling the particles for flow cytometry. Particle-bound scFv was detected using a DyLight650-conjugated anti-his6 antibody (Abcam, ab117504, diluted 1:300 in TBSA). rhTfR binding was detected by mouse anti-hTfR PE conjugate (FAB2474P, R&D systems, diluted 1:10 in TBSA). MFIs of the labeled beads were quantified using FlowJo; the bound rhTfR per scFv on the bead was determined as the ratio of PE fluorescence (TfR binding) divided by the DyLight650 fluorescence (scFv amount). Specific, pH-driven dissociation of rhTfR was then calculated by dividing the bound rhTfR per scFv at pH 5.5 by that at pH 7.4.

Immunocytochemistry

SKBR-3 cells were seeded on sterile 12 mm poly-D-lysine coated glass coverslips (BioCoat, Becton-Dickinson), housed in a 24-well plate, at 2×10$^5$ cells per well. Cells were cultured in 1 mL SKBR3GM for 24-72 h. prior to experimentation. Growth medium was aspirated, cells were washed once with DPBS containing 0.9 mM calcium chloride and 0.49 mM magnesium chloride (DPBSCM, Sigma-Aldrich), then 1.0 mL SFM containing 10 μM deferoxamine mesylate iron chelator (Sigma-Aldrich) was added. Cells were incubated at 37° C./5% $CO_2$ for 15 min to starve them of iron. Depending on the experimental goals, artificial dimers (ADs) or monomeric scFvs were used. ADs were created by pre-incubating purified scFv having c-myc epitope with either unconjugated or Alexa488-conjugated anti-c-myc antibody (clone 9E10, Covance or clone 9E10-A488, 16-308, EMD Millipore) at a 4:1 molar ratio in DPBS containing 10% goat serum (DPBS10G) as previously described [37]. After a 1 h. incubation at room temperature, ADs were diluted to 200 nM concentration in serum-free media (SFM is SKBR3GM above, without serum) and used for immunocytochemistry or flow cytometry as described below.

For immunocytochemistry, ADs or scFv at 200 nM concentration (300 μL total volume) were dosed onto live cells (iron-starved as above) and allowed to traffic for 2 h. at 37° C./5% $CO_2$. After trafficking the cells were washed with DPBSCM and fixed in 3.7% PFA, 4% sucrose for 15 min. at room temperature. Fixation was quenched by rinsing with DPBSCM containing 50 mM ammonium chloride. Cells were blocked with DPBS10G containing 1% BSA for 30 min at room temperature. Antibody incubations were all 1 h. at room temperature, and antibodies were diluted in DPBS containing 1% BSA. If intracellular antigens were to be stained, 0.1% saponin (Sigma) was added to the blocking and antibody dilution buffers. Primary antibodies used were anti-LAMP1 (Rabbit pAb, ab24170, Abcam, diluted 1:300), anti-EEA1 (Rabbit mAb, C45B10, Cell-Signaling, diluted 1:200), anti-LAMP2 (Mouse mAb, ab25631, diluted 1:300), and 9E10 (05-419, Millipore, 1:250). Secondary antibodies were all host species specific, and Alexa555 conjugated (Life Technologies, diluted 1:250). DAPI (Life Technologies) was used at 300 nM to visualize cell nuclei. Images were captured on an AxioImager-Z2 with a 63× oil-immersion objective (Zeiss). Meta z-stacks where created by automated fine, focal adjustment. Slice width was set to 1 μm, 10 slices were captured, and then reconstructed as a maximum intensity z-projection using ImageJ (v1.43u, NIH). Pearson co-localization coefficients were calculated from N≥2 independent, background subtracted images comprising 20-40 cells each using ImageJ (Fiji, www.fiji.sc) with the Coloc 2 plugin.

A variation of the immunocytochemistry procedure above was used to differentially visualize internalized versus surface-bound scFv. Since monomeric and artificially dimerized scFvs yielded indistinguishable intracellular distributions, AD's made with unconjugated anti-c-myc antibody were used for these experiments. Cells were cultured on 12 mm coated coverslips and prepared as described above. ScFv dimers at 200 nM were added to live cells and allowed to traffic for 1 h. at 37 C/5% $CO_2$. After trafficking, cells were washed three times in ice cold DPBS, fixed for 30 min. in ice-cold PFA. Cells were blocked for 30 min. at room temperature, and then incubated with anti-mouse-Alexa647 (diluted 1:500) for 30 min. at room temperature to label extracellular scFv. Next, the cells were permeabilized for 10 min. with DPBS containing 0.2% Triton X-100. Finally, to visualize intracellular scFv dimers, permeabilized cells were incubated for 30 min. at room temperature with anti-mouse-Alexa488 (diluted 1:500) which had been diluted in DPBS10G containing 0.1% Triton X-100.

Flow Cytometric Quantification of Cell-Associated scFv

SK-BR-3 were seeded at a density of 1×10$^5$ cells per well in 48 well TC-treated plates and grown 48 h. in advance for flow cytometry. Growth medium was aspirated, cells were washed once with DPBS containing 0.9 mM calcium chloride and 0.49 mM magnesium chloride (DPBSCM, Sigma-Aldrich), then 0.5 mL SFM containing 10 μM deferoxamine mesylate iron chelator (Sigma-Aldrich) was added. Cells were incubated at 37° C./5% $CO_2$ for 15 min to starve them of iron. After iron starvation, cells were washed once in DPBSCM and saturating concentrations of AD were added, 125 μL of 200 nM AD. Cells were incubated at 37° C./5% $CO_2$ for 2 h. to allow the ADs to traffic. For experiments involving inhibition of intracellular acidification, 200 nM of bafilomycin A1 (BafA1) (Santa Cruz) was added in SFM and incubated with cells for 45 min, prior to the iron chelation step. The reminder of the experimental steps were identical to those denoted above with the addition of 200 nM BafA1 to each solution. Following trafficking, the AD solution was aspirated and the cells were washed twice with DPBSCM. For quantification of total-cell associated antibody, cells were detached by incubation with non-enzymatic cell dissociation buffer (Gibco). To quantify the internalized antibody fraction only, extracellular protein degradation and cell detachment were achieved simultaneously by incubation with 0.25% Trypsin-EDTA solution (Gibco). In either case, detached cells were transferred into 3 mL of ice-cold DPBS10G and immediately centrifuged at 180×g for 5 min. Cells were resuspended in 300 μL fixation buffer (3.7% PFA, 4% sucrose) and incubated for 10 min at room temperature before being quenched with 3 mL DPBS containing 50 mM ammonium chloride and centrifuged once more at 180×g for 5 min. Cells were resuspended for flow cytometry in 500 μL DPBS containing 20 g/L BSA and 2 mM EDTA. Cells of normal size and morphology were gated and the MFI in the Alexa488 channel was quantified using FlowJo. MFI data from trypsinized cells corresponded to the internalized fraction of scFv, while data from non-enzymatically detached cells corresponded to total cell-associated scFv. Surface fraction was calculated by subtracting the internalized signal from the total signal. Non-specific background signal equal to the MFI of scFv D1.3 treated cells was subtracted from all samples, MFI values were normalized intra-day to total cell-associated H7, and the experiment was repeated on multiple days.

Statistics

For all calculations in this manuscript, data from multiple independent experiments on each of a minimum of two days were collectively used to determine quantitative parameters, their associated 95% confidence intervals (95% CI), and significance levels (p-value) by student's t-test. The resultant total number of independent experiments (n-value) for each assay is denoted in each respective figure legend.

Results

Assessment of scFv H7 pH-Sensitivity and Histidine Mutagen

As a first step in engineering pH-sensitive TfR binding, the intrinsic pH-sensitivity of wild-type anti-human TfR scFv H7 was established using a yeast surface display dissociation assay (FIG. 1B). After saturation of yeast-displayed H7 with recombinant human TfR (rhTfR) at neutral pH, yeast were exchanged into acidic buffer (pH 4.0-6.5) for 10 minutes to allow for TfR dissociation, and the fraction of TfR remaining bound was assessed by flow cytometry. H7 was found to dissociate from TfR in a pH-dependent manner, particularly at pH 5.0 and below where TfR binding was almost completely abolished (FIG. 1B, histogram). However, at pH 5.5, TfR binding was decreased by just 44% compared to the level observed at pH 7.4 (FIGS. 1B, 2, and 3A). Thus, there was a clear opportunity for engineering scFvs having a more rapid (<10 min) dissociation from TfR at pH 5.5, conditions chosen based on their relevance to endogenous transferrin-TfR trafficking [19, 20, 38].

Figures 2A, 2B, 2C, 2D, 2E, 2F, 2G, 2H:
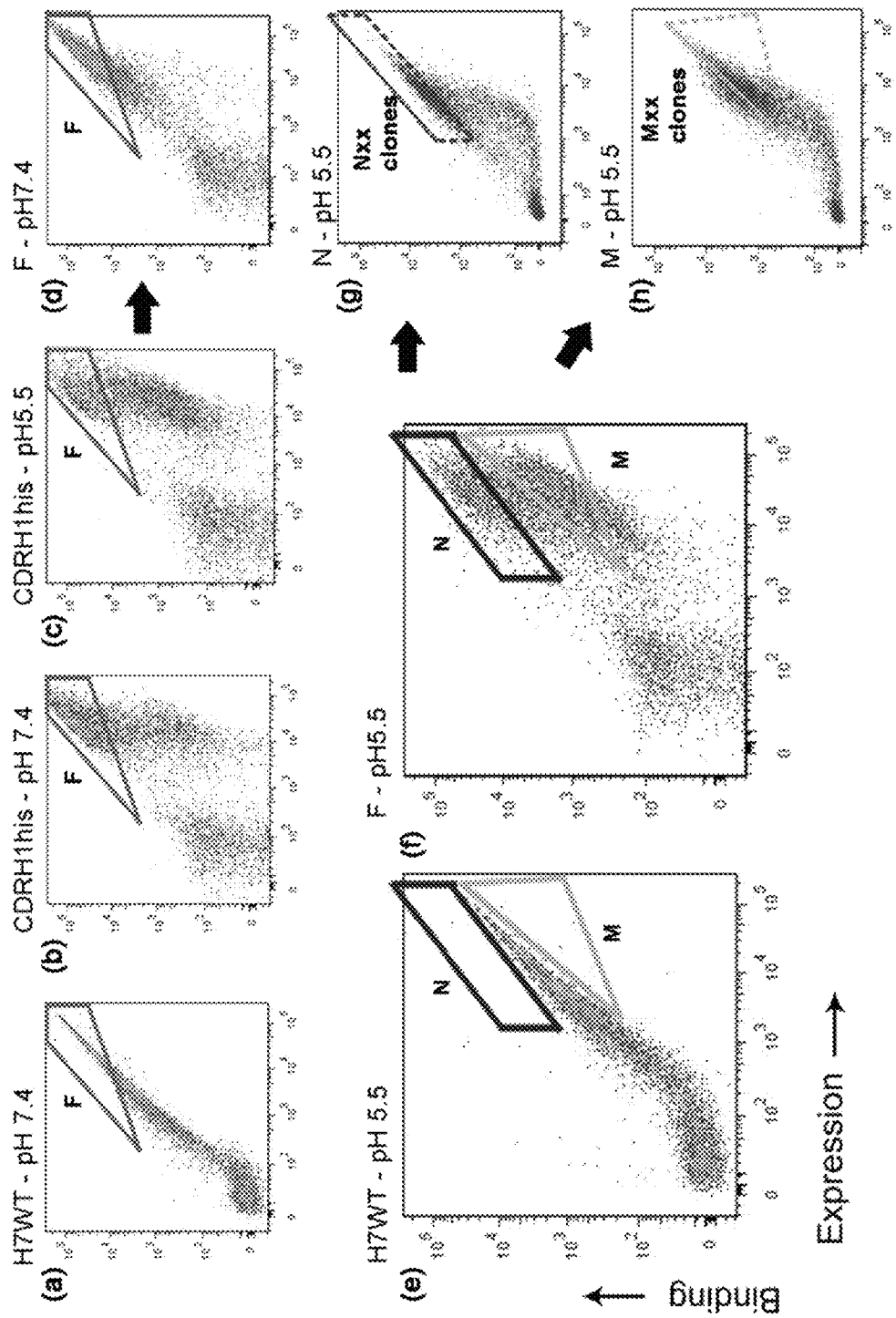
Figure 3A:
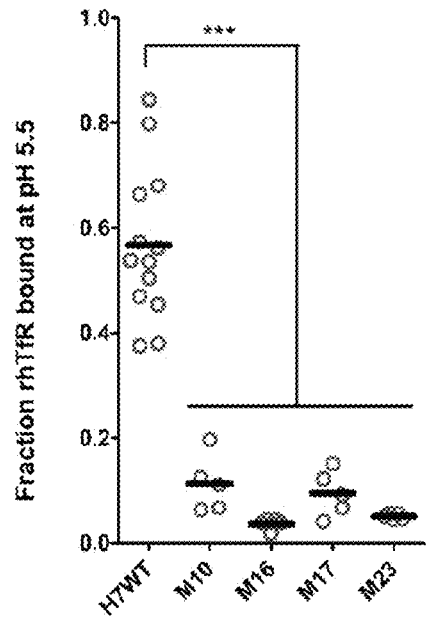
FIG. 3A: Fraction TfR bound to M mutants after 10 minute incubation at pH 5.5. (n=5 for M mutants and n=13 for H7, and *, p<0.001)

FIG. 2(A-H) shows flow-cytometric screening of the CDRH1his library for scFvs having affected dissociation from TfR at pH 5.5. Dot plots depict the behavior of the various scFv populations after saturation with rhTfR followed by a 10 minute dissociation step in pH 5.5 or 7.4 buffers. TfR-binding is indicated on the y-axis while scFv surface expression level is indicated on the x-axis. Sample gates are drawn for illustrative purposes. FIG. 2A shows antigen binding and expression of wild-type H7 at pH 7.4. As shown in FIG. 2B and FIG. 2D, pool F was derived from the CDRH1his library via two rounds of sorting at pH 7.4 and comprises neutral pH TfR-binders. As shown in FIG. 2C (also FIG. 7), a population comprising pH-insensitive binders exists in CDRH1his and can be visualized in gate F after the library is subject to pH 5.5 dissociation. FIG. 2E shows antigen binding and expression of wild type H7 at pH 5.5. As shown in FIG. 2F, both pools M and N were obtained by selecting for different populations within pool F, post dissociation at pH 5.5. As shown in FIG. 2F and FIG. 2G, gate N was placed near the maximum in TfR-binding signal to select for pH-insensitive scFvs and ultimately yielded pool N. As shown in FIG. 2F and FIG. 2H, alternatively, gate M was placed just above the no-antigen control, but below gate N to select for the pH-sensitive binders ultimately found in pool M (see also FIG. 7). As shown in FIG. 2G and FIG. 2H, dotted gates are drawn in the panels depicting flow-cytometric analysis of the M and N pools, to show the origin of clones listed in Table 1. Further detailed explanation of the screening strategy and pools depicted in the various panels can be found in the text.

Figure 3B:
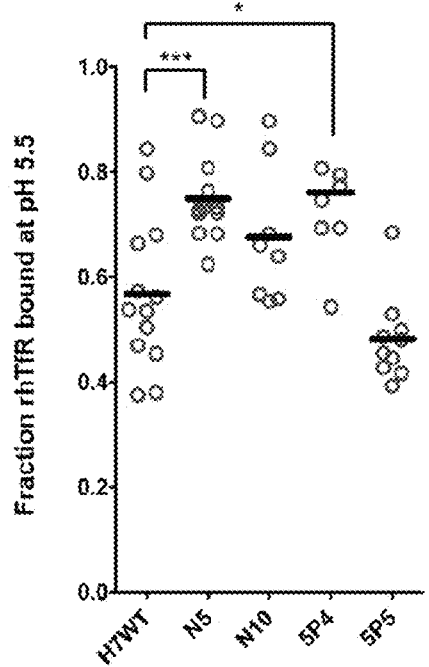
FIG. 3B: Fraction TfR bound to N and 5P mutants after 10 minute incubation at pH 5.5. (n=8 for N and 5P mutants and n=13 for H7 mutant as in panel a) and *, p<0.001 *, p<0.05).
Figure 3C:
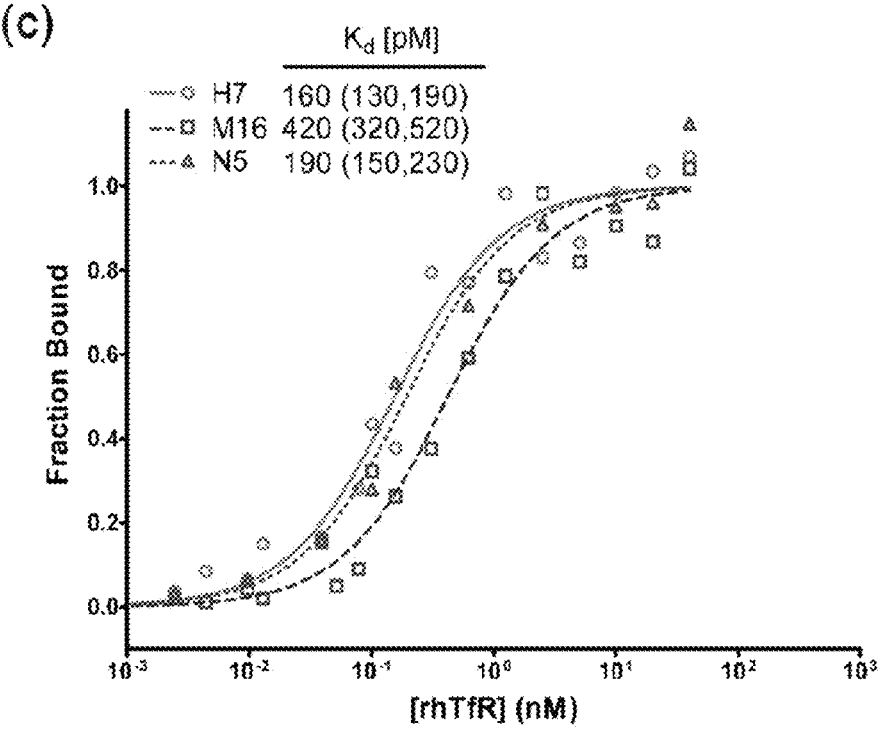
FIG. 3C: Apparent equilibrium binding affinity of select clones on the surface of yeast at pH 7.4. Mean data from five independent experiments are plotted along with the fitted equilibrium binding isotherms. The legend shows numeric values for the best-fit equilibrium binding affinity (Kd) and associated 95% CI.
Figure 4A:
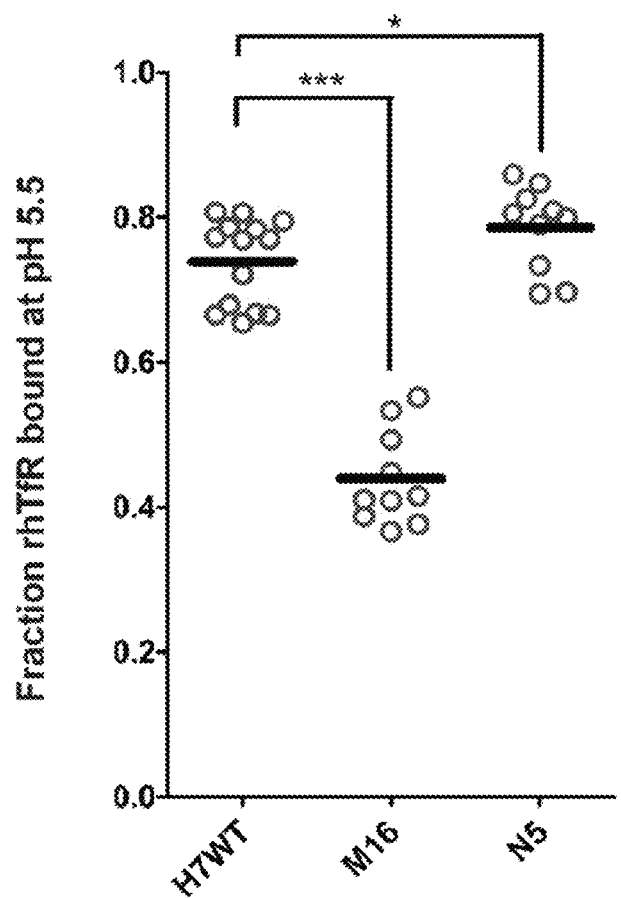
FIG. 4A: Magnetic bead assay to determine the pH-sensitivity of TfR-binding using soluble protein. Soluble scFvs were captured on the bead surface via their c-myc epitope tags and incubated with rhTfR. After 10 minute incubation in pH 7.4 or pH 5.5 buffer, the fraction of TfR bound at pH 5.5 versus pH 7.4 was assayed by flow cytometry. (n=10 for M16, n=14 for H7 and n=10 for N5, ***, p<0.001, *, p<0.05)
Figure 4B:
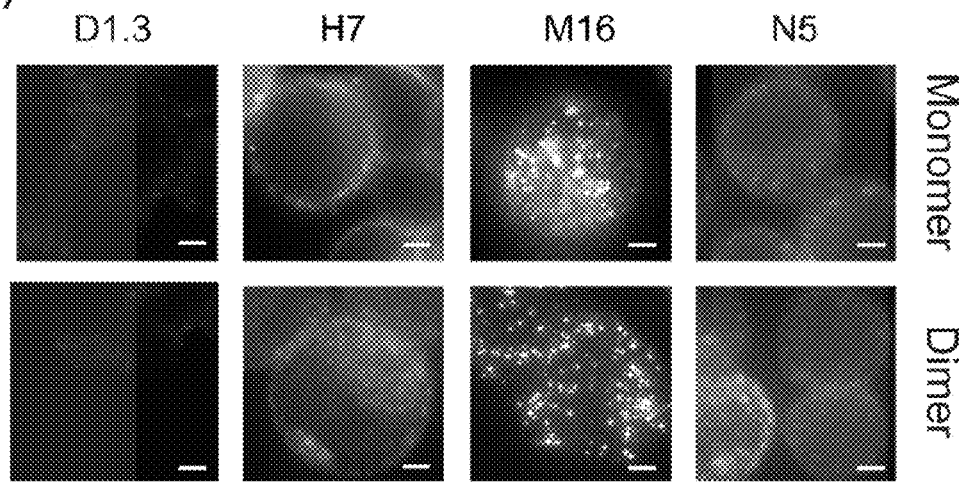
FIG. 4B: Whole-cell immunolabeling using monomeric scFvs and artificial scFv dimers formed via the scFv c-myc epitopes as described in Materials and Methods. Proteins were allowed to traffic for 2 hours in SK-BR-3 cells at 37° C. Meta-z stacks were captured and recombined into a maximum intensity z-projection to better visualize surface versus intracellular protein. Scale bars=5 μm.

FIG. 3(A-C) shows quantitative analysis of scFvs isolated from the CDRH1his library using yeast surface display. FIG. 3A shows fraction TfR bound to M mutants after 10 minute incubation at pH 5.5. (n=5 for M mutants and n=13 for H7, and *, p<0.001) FIG. 3B shows fraction TfR bound to N and 5P mutants after 10 minute incubation at pH 5.5. (n=8 for N and 5P mutants and n=13 for H7 mutant as in panel a) and *, p<0.001 *, p<0.05). FIG. 3C shows apparent equilibrium binding affinity of select clones on the surface of yeast at pH 7.4. Mean data from five independent experiments are plotted along with the fitted equilibrium binding isotherms. The legend shows numeric values for the best-fit equilibrium binding affinity (Kd) and associated 95% CI Previously, a number of scFv H7 variants were isolated possessing improved equilibrium binding affinity at neutral pH [33]. Sequence analysis of randomly selected clones from the affinity-matured pools revealed a strong bias (20 out of 27 unique mutations) toward amino acid changes in the heavy chain, including CDRH1 and CDRH2 [33], suggesting a direct role for each of these two CDRs in TfR binding. However, amongst mutations affecting the most substantial affinity enhancement, those located in CDRH2 predominated, indicating a comparatively important role for CDRH2 in mediating TfR binding at neutral pH. Thus, CDRH1 was chosen as a locus for engineering an scFv with increased dissociation from TfR at pH 5.5. Given that multiple histidine substitutions in combination have been shown to be particularly effective at imparting pH-sensitive antigen binding [39], a recombinant library was designed to saturate CDRH1 with all combinations of histidine, from a single histidine at each position to ten consecutive histidines (FIG. 1a and Materials and Methods). The resulting H7 CDRH1his yeast display library comprised $3 \times 10^7$ clones and substantially oversampled the theoretical diversity ($1.8 \times 10^5$) arising from designed nucleotide degeneracy. Sequencing of 12 randomly selected clones from the unselected library indicated a rich mix of histidine mutations in CDRH1, both in number and position (Table 1).

Screening the CDRH1his Library

The CDRH1his library was screened by TfR saturation of surface-displayed scFvs followed by 10 minutes of TfR dissociation at pH 5.5 (FIG. 1B). Evaluating the response (full length-display and antigen binding) of the starting library to this treatment yielded two key observations. First, at pH 7.4, approximately 40% of the library clones retained substantial TfR binding despite mutations to the CDRH1 loop (FIG. 2B, gate F). Second, when incubated at pH 5.5 for 10 minutes, many of the clones dissociated from TfR as desired, but a sizable population (~20%) remained bound (FIG. 2C, gate F). H7 was comparatively less responsive to pH 5.5 treatment (FIG. 2E and FIG. 7). Given these responses, we proceeded to screen for both pH-insensitive and pH-sensitive mutants.

Figures 7A, 7B, 7C:
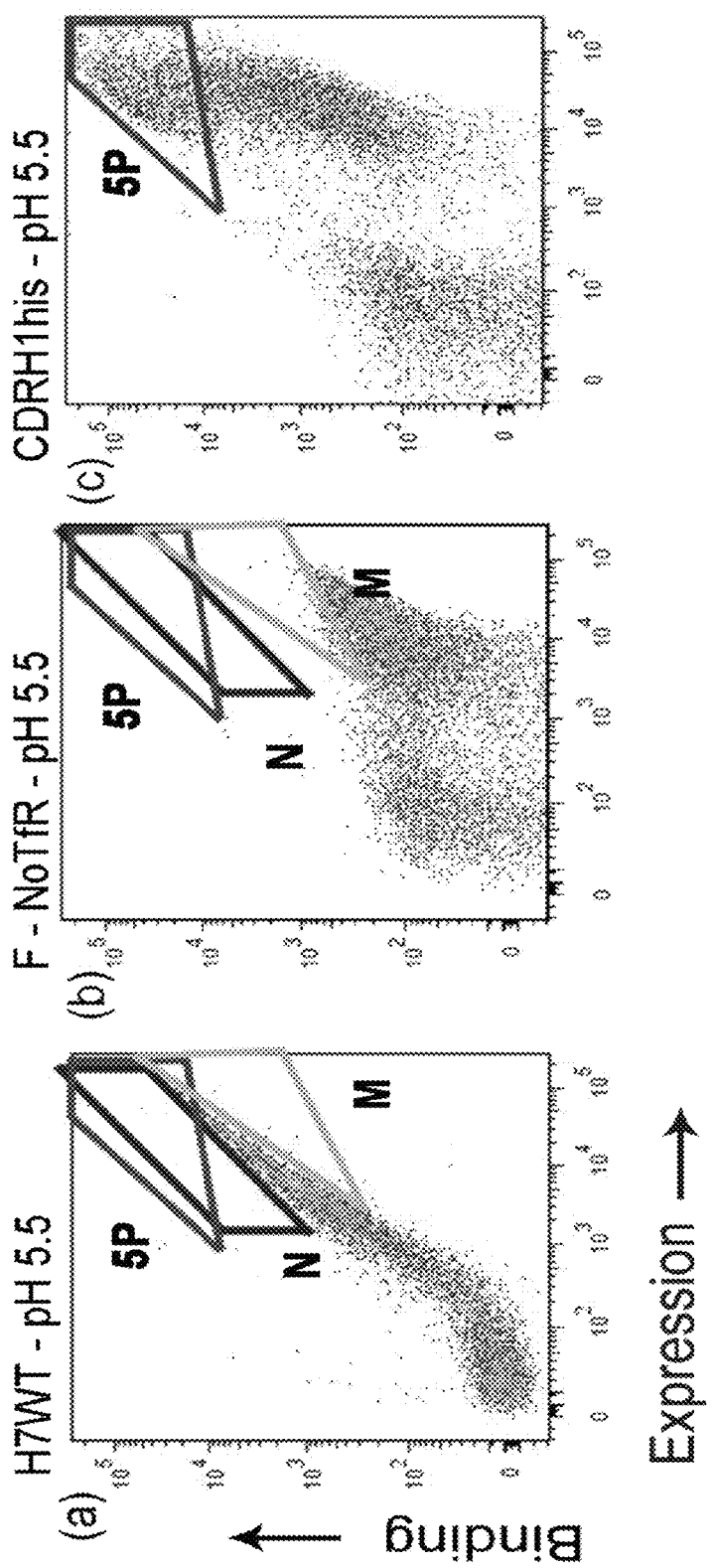
FIG. 7A and FIG. 7B: In the first two panels, dot plots of H7+TfR and pool F−TfR are shown after pH 5.5 antigen dissociation treatment.
FIG. 7C: CDRH1his library after pH 5.5 dissociation. The binding signal of H7, Pool F and CDRH1his at pH 5.5 provided reference points for sorting of the 5P, N and M pools. Gates are drawn for illustrative purposes. Pool 5P was derived from four rounds of sorting CDRH1his, selecting for scFvs that maintained binding at pH 5.5.

FIG. 7(A-C) shows flow cytometric screening of the CDRH1his library for scFvs lacking pH 5.5 sensitivity. As shown in FIG. 7A and FIG. 7B, in the first two panels, dot plots of H7+TfR and pool F−TfR are shown after pH 5.5 antigen dissociation treatment. FIG. 7C shows CDRH1his library after pH 5.5 dissociation. The binding signal of H7, Pool F and CDRH1his at pH 5.5 provided reference points for sorting of the 5P, N and M pools. Gates are drawn for illustrative purposes. Pool 5P was derived from four rounds of sorting CDRH1his, selecting for scFvs that maintained binding at pH 5.5.

Since it was desired to maintain anti-TfR potency at neutral pH, two initial rounds of FACS-based sorting were performed at pH 7.4 to purify TfR binders from the CDRH1his library (FIG. 2B, gate F). The resulting functional pool, "F", was essentially free from scFv mutants with impaired TfR binding at neutral pH (FIG. 2D), while still containing scFvs capable of the desired TfR dissociation at pH 5.5 (FIG. 2f). Subsequently, to isolate pH-sensitive TfR binders, pool F was sorted using gate "M", bracketed on the high end by the H7, pH 5.5 TfR binding signal, and on the low end by the no-antigen control (FIGS. 2E-F and 7). Two rounds of FACS sorting in this fashion, yielded pool "M", a population with significantly attenuated TfR binding after 10 minutes at pH 5.5 (FIG. 2H). In parallel, a second non-overlapping gate, N, was added above the M gate. Clones in pool "N" exhibited increased retention of TfR binding compared to H7 at pH 5.5 (FIGS. 2G and 7). In contrast to the pH-sensitive M pool, clones in the N pool maintained strong association with TfR at pH 5.5 and represented a class of pH-insensitive, TfR binding, scFvs. Finally, pH-insensitive binders were isolated directly from the CDRH1his library without going through the F pool as an intermediate (FIG. 7). These clones possessed properties similar to pool N and were referred to as 5P.

Clonal scFv Analysis from M, N, and 5P Pools

A combined 92 clones from the M, N, and 5P pools were screened for TfR binding at pH 7.4 and extent of dissociation after 10 minutes at pH 5.5. Those clones exhibiting the desired pH sensitivity (M) or insensitivity (N and 5P) were sequenced to evaluate histidine substitution in the engineered CDRH1s. The pattern of histidine substitution in unique clones from pH sensitive pool M was distinct from that found in the N and 5P clones with a strong bias toward histidine in at least three of the central positions (VH31-VH34) of CDRH1 (Table 1). Additionally, this central histidine core was accompanied by the mutation of at least one of the adjacent residues (VH30 or VH35) to proline in the majority of the M clones (e.g. Table 1, clones M8 and M16). In contrast, none of the unique clones analyzed from the pH-insensitive N or 5P pools contained either of these features. Instead, the wild-type serines at VH32 and VH33 were often mutated to arginine or asparagine, with any newly added histidines appearing away from the VH31-VH34 "core" at either VH30 or VH35 (e.g. clones N4 and 5P4 in Table 1c). N and 5P series clones also had, on average, fewer total mutations than their M series counterparts (37% versus 64%), and a wild-type tyrosine at position VH34 that remained invariant.

Based on these general mutational classes, four pH-sensitive (M10, M16, M17, and M23) and four pH-insensitive (N5, N10, 5P4, and 5P15) mutants were quantitatively assayed for fractional TfR dissociation at pH 5.5. For reference, wild-type scFv H7 retained 56% of bound TfR after the 10 minutes pH 5.5 incubation (FIG. 3A). All of the M clones exhibited greater than 90% dissociation in this same timeframe (FIG. 3A, $p<0.001$). Two of the N and 5P clones exhibited some modest reduction in association; clones N5 (75±5% bound, $p<0.001$) and 5P4 (76±11% bound, $p<0.05$) retained roughly 25% more bound TfR during low pH incubation than H7 (FIG. 3B).

Due to the significant number of mutations in CDRH1 (Table 1), we measured the apparent equilibrium binding affinity at pH 7.4 for the leading pH-insensitive (N5) and pH sensitive (M16) clones. As shown in FIG. 3*c*, N5 exhibited a statistically equivalent apparent equilibrium binding affinity (190±40 pM) compared to H7 (160±30 pM). M16 possessed a 2.5-fold attenuated equilibrium binding affinity (420±100 pM). Thus, the apparent affinities of M16 and N5 both remained sub-nanomolar although CDRH1 was substantially mutated.

Characterization of pH-Dependent scFvs

The 16 scFvs from M, N, and 5P pools listed in Table 1 were secreted from yeast as soluble scFvs. Of these, only clones M16 and N5 could be expressed and purified in amounts sufficient to allow further characterization, indicating that certain CDRH1 mutations, alone or in concert, could negatively impact scFv secretion. Maintenance of pH-sensitive and pH insensitive TfR binding was evaluated for scFvs M16 and N5, respectively, through capture of soluble antibody onto rhTfR-coated beads followed by low-pH dissociation and flow cytometric analysis. The rank ordering of pH sensitivity was consistent with that observed in the yeast surface display format, although less overall dissociation from rhTfR was observed using this assay. ScFv M16, retained 44±5% of TfR binding after 10 minutes of pH 5.5 incubation versus 74±3% for WT H7 (FIG. 4*a*, $p<0.001$), while the pH-insensitive clone, scFv N5, retained slightly more TfR-binding than H7 (FIG. 4*a*, 80±4% $p<0.05$)

FIGS. 4(A and B) shows analysis of soluble M16, N5 and H7 scFvs. FIG. 4A shows magnetic bead assay to determine the pH-sensitivity of TfR-binding using soluble protein. Soluble scFvs were captured on the bead surface via their c-myc epitope tags and incubated with rhTfR. After 10 minute incubation in pH 7.4 or pH 5.5 buffer, the fraction of TfR bound at pH 5.5 versus pH 7.4 was assayed by flow cytometry. (n=10 for M16, n=14 for H7 and n=10 for N5, ***, $p<0.001$, *, $p<0.05$) FIG. 4B shows whole-cell immunolabeling using monomeric scFvs and artificial scFv dimers formed via the scFv c-myc epitopes as described in Materials and Methods. Proteins were allowed to traffic for 2 hours in SK-BR-3 cells at 37° C. Meta-z stacks were captured and recombined into a maximum intensity z-projection to better visualize surface versus intracellular protein. Scale bars=5 μm.

Given that the TfR dissociation behavior of M16 and N5 was distinct from wild-type H7, both in surface-displayed and soluble forms, we next explored whether pH-sensitive TfR binding could alter intracellular antibody trafficking. When applied to the human breast cancer cell line (SK-BR-3), scFvs bound to the cell surface and were internalized. Monomeric scFvs were dosed onto SK-BR-3 cells and incubated at 37° C. for 2 hours to allow for binding and internalization. H7 and N5 tended to bind the periphery of cells, with some punctate localization just inside the cell membrane compared to M16 which had reduced surface labeling in favor of distinct, intracellular structures with qualitatively elevated concentrations of scFv (FIG. 4B). If scFvs were first pre-dimerized, a similar distribution was observed (FIG. 4B). A two fluorophore immunolabeling procedure was employed to unequivocally demonstrate binding and internalization of M16, N5 and H7. As suggested by the single color immunolabeling (FIG. 4B), binding and internalization were both clearly observed for each scFv (FIG. 5A). The intracellular staining for scFv M16 was unique, however, showing a significant number of large, punctate, vesicular structures, while H7 and N5 yielded smaller membrane localized structures (FIG. 5A).

FIGS. 5(A and B) shows endocytosis of scFvs into SK-BR-3 cells and quantification of intracellular accumulation. FIG. 5A shows immunolabeling of surface and internalized scFvs. Soluble scFvs were dimerized via their c-myc epitope tags and pulsed onto SK-BR-3 cells at 37° C. for 2 hours to allow for internalization. Fluorophores with different emission spectra were used to immunolabel surface-bound scFv (Alexa647, pseudo-colored pink) and, after permeabilization, intracellular scFv (Alexa488, pseudo-colored green). Nuclei were visualized with DAPI (pseudo-colored blue). Arrowheads indicate the distinct pattern of internalized scFv M16. Scale bar is 5 μm. FIG. 5B shows quantification of scFv association with SK-BR-3 cells. scFv pre-dimerized with 9E10-Alexa488 was dosed onto live SK-BR-3 cells and allowed to traffic at 37° C. for 2 hours (see Materials and Methods in the Example for assay details) and total cell-associated scFv assayed by flow cytometry. Internalized scFv was also quantified by flow cytometry after removal of the cell surface bound scFv by trypsinization. Total cell-associated scFv is normalized to H7 scFv and internalized and surface scFv sum to the totals for each clone. (n=8 for H7 and M16 and n=12 for N5, ***, $p<0.001$).

Figure 5A:
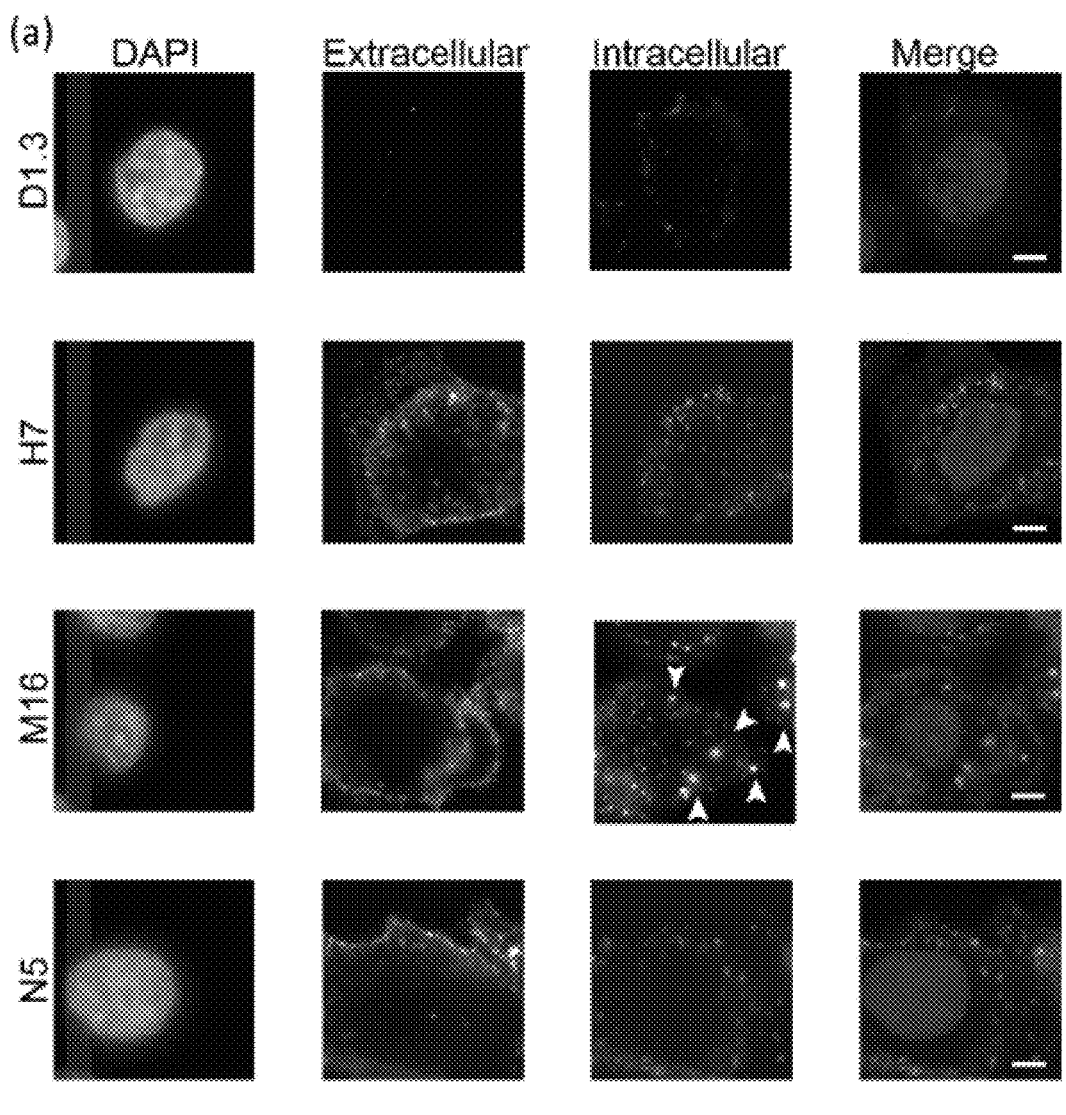
FIG. 5A: Immunolabeling of surface and internalized scFvs. Soluble scFvs were dimerized via their c-myc epitope tags and pulsed onto SK-BR-3 cells at 37° C. for 2 hours to allow for internalization. Fluorophores with different emission spectra were used to immunolabel surface-bound scFv (Alexa647, pseudo-colored pink) and, after permeabilization, intracellular scFv (Alexa488, pseudo-colored green). Nuclei were visualized with DAPI (pseudo-colored blue). Arrowheads indicate the distinct pattern of internalized scFv M16. Scale bar is 5 μm.
Figure 5B:
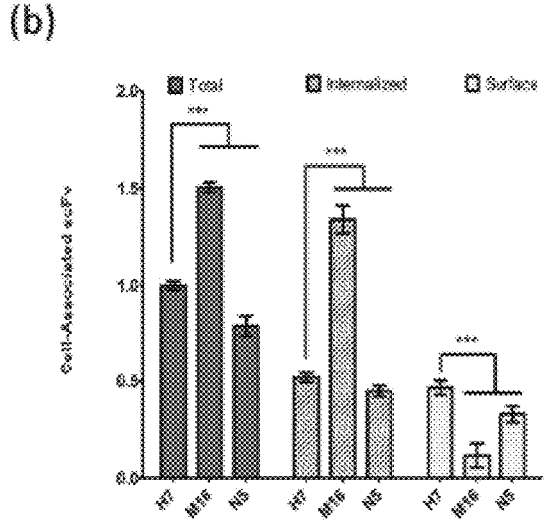
FIG. 5B: Quantification of scFv association with SK-BR-3 cells. scFv pre-dimerized with 9E10-Alexa488 was dosed onto live SK-BR-3 cells and allowed to traffic at 37° C. for 2 hours (see Materials and Methods in the Example for assay details) and total cell-associated scFv assayed by flow cytometry. Internalized scFv was also quantified by flow cytometry after removal of the cell surface bound scFv by trypsinization. Total cell-associated scFv is normalized to H7 scFv and internalized and surface scFv sum to the totals for each clone. (n=8 for H7 and M16 and n=12 for N5, *, p<0.001).
Figure 5C:
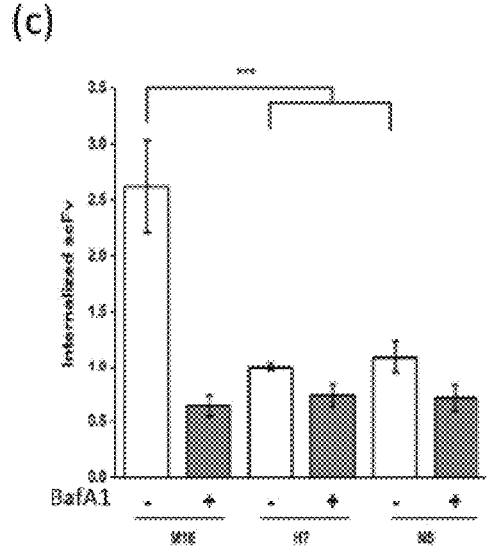
(FIG. 5C) Quantification of scFv internalization after pre-treatment with endosomal acidification inhibitor, BafA1. Internalized scFv was normalized to that for wild-type H7 in the absence of BafA1 treatment. (n=6 for H7, M16 and N5, *p<0.001).

Next, the effects of pH-sensitive TfR binding on the total cell-association and endocytosis of the engineered scFvs were quantitatively assessed by flow cytometry. Compared to H7, N5 had, on average, 20% less total cellular association (FIG. 5B, p<0.001), while the levels of total cellular association for scFv M16 were 1.5-fold higher (FIG. 5B, p<0.001). To directly quantify the internalized fraction, we capitalized on the fact that TfR contains a membrane-proximal trypsin cleavage site which can be used to remove surface exposed TfR along with any scFv that might be bound [40]. When trypsinized cell samples were assayed by flow cytometry the levels of internalized scFv M16 were 2.6-fold greater than wild-type H7 as a result of more total cellular association (1.5-fold) and a higher fraction of cell-associated scFv being found internally (87%) (FIG. 5b, p<0.001). N5 and H7 on the other hand, were quite similar in terms of percentage of total cell-associated scFv internalized (FIG. 5B, 52% of total H7 was internalized, and 56% of total N5 was internalized). Taken together, these data confirmed the enhanced internalization of M16 compared with N5 and H7 as previously suggested qualitatively by the immunocytochemistry images. In order to examine whether pH-dependent phenomena were driving the difference in increased scFv M16 internalization, the amount of internalized scFv was monitored after treatment with bafilomycin A1 (BafA1), an inhibitor of endosomal-lysosomal acidification [41,42]. In contrast with the untreated, control samples where scFv M16 internalized at levels 2.5-fold greater than wild-type H7 (FIG. 5c, p<0.001), treatment with BafA1 completely removed the beneficial effects of M16 on internalization such that it showed no difference in internalization in comparison to wild-type H7 or scFv N5 (FIG. 5c, p>0.05). These results indicate that endosomal acidification is required to observe the beneficial internalization properties of M16, confirming the important role of pH-sensitive binding.

Figures 6A, 6B, 6C, 6D:
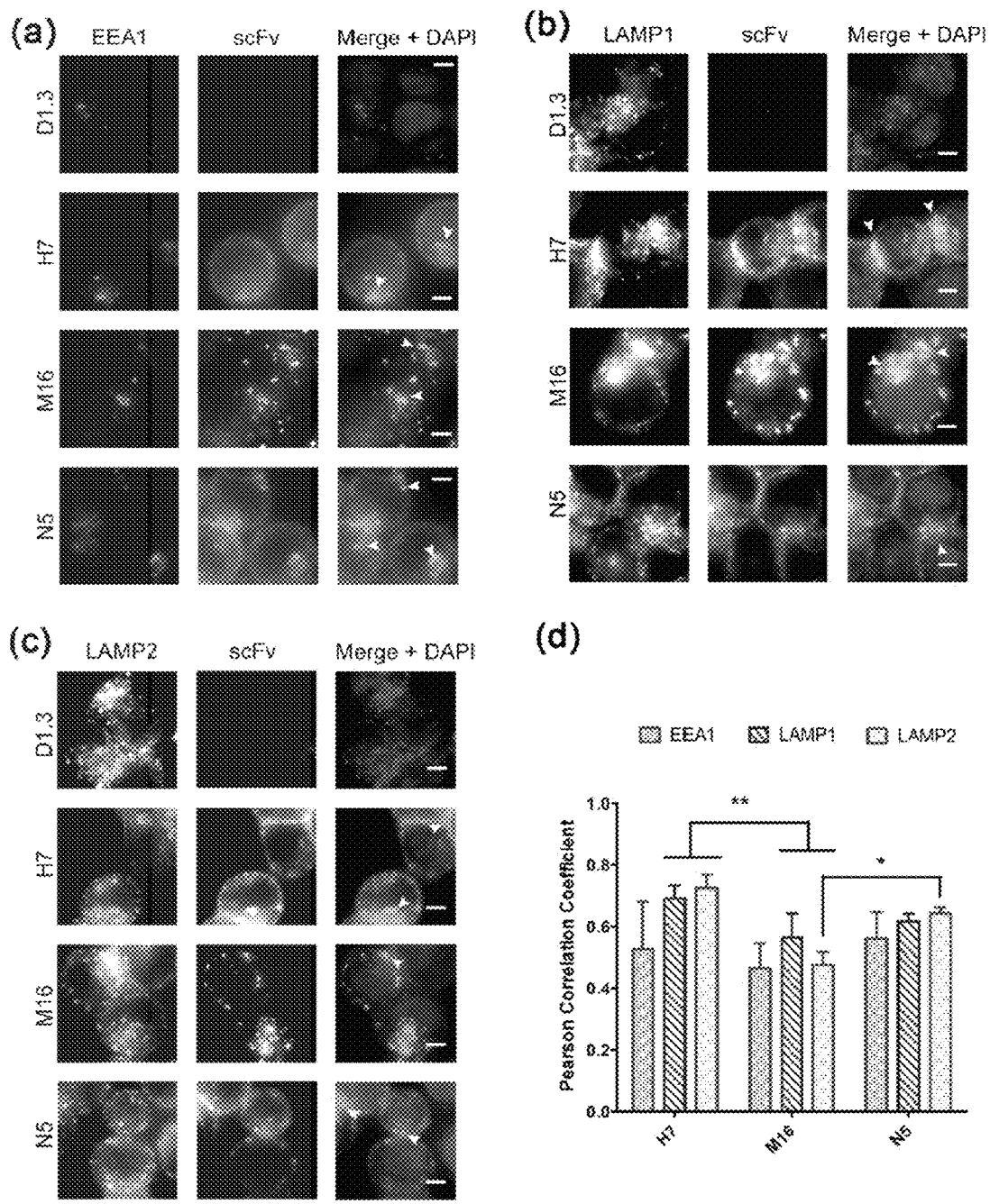
FIG. 6A: SK-BR-3 cells which had been allowed to endocytose scFv dimers (green in merged) were counterstained with an antibody against early endosome antigen type 1 (EEA1, red in merged).
FIG. 6B and FIG. 6C: The same steps were used to counterstain with antibodies against lysosomal associated membrane proteins 1 and 2 (LAMP1 and LAMP2, red in merged). As indicated by arrowheads, all scFvs co-localized with EEA1, LAMP1 and LAMP2. Scale bar is 5 μm.
FIG. 6D: Co-localization with EEA1, LAMP1, and LAMP2 was quantified by Pearson correlation coefficient (**, p<0.01, *, p<0.05).

Finally, the co-localization of internalized scFvs with markers of intracellular compartments was evaluated to determine what alterations in antibody trafficking were responsible for the increased internalization behavior of M16. H7, M16 and N5, all showed isolated areas of co-localization with the endosomal marker EEA1 (FIG. 6A), and the late endosomal/lysosomal markers LAMP1 (FIG. 6B) and LAMP2 (FIG. 6C). Quantitative co-localization analysis did not suggest that pH-sensitivity dramatically shifted trafficking away from the lysosome (LAMP1 or LAMP2) and towards the endosome (EEA1), or vice versa (FIG. 6D). Instead, the Pearson correlation coefficients suggested that co-localization of pH-sensitive M16 with each of the three intracellular markers was uniformly reduced compared with either H7 or N5, although only differences in LAMP1 and LAMP2 coefficients were statistically significant (FIG. 6D, p<0.01). Reflective of the uniform reduction in co-localization with endosomal and lysosomal markers, the discrete foci of accumulated M16 within the cells did not visually appear to localize strongly with any of the markers tested (FIG. 6A-C).

FIG. 6(A-D) shows intracellular co-localization of scFvs with endosomal and lysosomal markers. FIG. 6A shows SK-BR-3 cells which had been allowed to endocytose scFv dimers (green in merged) were counterstained with an antibody against early endosome antigen type 1 (EEA1, red in merged). As shown in FIG. 6B and FIG. 6C, the same steps were used to counterstain with antibodies against lysosomal associated membrane proteins 1 and 2 (LAMP1 and LAMP2, red in merged). As indicated by arrowheads, all scFvs co-localized with EEA1, LAMP1 and LAMP2. Scale bar is 5 μm. As shown in FIG. 6D, co-localization with EEA1, LAMP1, and LAMP2 was quantified by Pearson correlation coefficient (**, p<0.01, *, p<0.05).

Discussion

Antibodies with the ability to respond to endosomal pH are intriguing because they offer an additional, tunable, layer of functionality beyond antigen binding affinity. Through semi-rational histidine saturation mutagenesis of parental anti-TfR scFv H7, combined with rapid screening via yeast surface display, it was possible to engineer appreciable increases in dissociation from TfR at pH 5.5, while largely maintaining pH 7.4 antigen binding. In particular, mutant M16 displayed increased overall cellular association primarily resulting from increased intracellular accumulation, and a substantially different intracellular distribution compared to wild-type H7 or the pH-insensitive mutant N5.

Here, we embraced the idea that pH-sensitivity results from multiple mutations acting in concert [41], especially from multiple histidines in close proximity [39, 42-44]. After screening the histidine-saturated CDRH1 library, we found that the resulting pH-sensitive scFvs contained three or more histidines (out of 10 total residues), centrally located in CDRH1, supporting the beneficial effect of multiple proximal histidines for pH-responsiveness (Table 1). The protonation of the histidine residues at pH 5.5 drives an increased dissociation, also indicating that the CDRH1 loop likely participates in antigen binding as predicted prior to library design [33]. In addition, to achieve the multiplicity of histidine mutations that were key to the outcomes presented above, histidine saturation mutagenesis provides the most efficient approach. Our results were mirrored by an engineered version of the therapeutic IgG adalimumab, where the synergistic effect of paired histidine mutations in CDRs imparted pH-sensitive antigen binding [45]. The context of histidines within the antigen binding site is also an important factor as evidenced by an anti-HER2 Fc-Ab where pH-sensitivity resulted from non-histidine mutations proximal to wild-type histidines [46]. Given the prevalence of three or more histidine mutations in pH-responsive clones, the context-driven effects of such bystander mutations likely played less of a role in our study.

After binding at pH 7.4, scFv M16 accumulates at significantly higher levels than H7 or its pH-insensitive counterpart N5. As described above, models of anti-TfR immunotoxin delivery have pointed to TfR dissociation as an influential parameter in predicting increased cell-association [24, 25]. The data presented here strongly suggest that pH-dependent TfR dissociation properties of M16 lead to its distinct phenotypic properties. Since assays were performed at scFv concentrations capable of saturating cell surface TfR, the observed differences in internalization phenotype stemmed from differences in intracellular interactions.

In order to examine whether pH-dependent phenomena were driving the difference in increased scFv M16 internalization, the amount of internalized scFv was monitored after treatment with bafilomycin A1 (BafA1), an inhibitor of endosomal-lysosomal acidification [41, 42]. In contrast with the untreated, control samples where scFv M16 internalized at levels 2.5-fold greater than wild-type H7 (FIG. 5c, p<0.001), treatment with BafA1 completely removed the beneficial effects of M16 on internalization such that it showed no difference in internalization in comparison to wild-type H7 or scFv N5 (FIG. 5c, p>0.05). These results indicate that endosomal acidification is required to observe the beneficial internalization properties of M16, confirming the important role of pH-sensitive binding.

Endocytosed M16, H7, and N5 all co-localized with EEA1, LAMP1, and LAMP2 (FIG. 6A-C), frequently cited markers of early-endosomes and late-endosomes/lysosomes, respectively. Quantitative image analysis did not indicate an obvious shift in endosomal versus lysosomal trafficking for M16 (FIG. 6D) compared to H7 or N5. However, an overall reduction in co-localization for all markers was observed. The reduction in M16 co-localization with LAMP1 and LAMP2 correlates with previous findings where reduced anti-TfR affinity, anti-TfR avidity or pH-sensitive TfR binding led to a reduction in lysosomal association [47, 50, and 51]. Also, the reduction in M16 association with endosomal and lysosomal markers occurred in concert with the appearance of large vesicular structures that did not co-localize with any of the markers tested, suggesting a divergence in trafficking. Of interest, when previous studies compared a pH-insensitive anti-TfR antibody (128.1) to a pH-sensitive antibody (MEM-189), 128.1 was found to co-localize with CD63 (late endosomal/lysosomal maker) while MEM-189 instead accumulated in large intracellular structures, reminiscent of those observed with M16, that did not co-localize with CD63 [47]. In the future, more comprehensive trafficking analysis will be needed to definitively pinpoint the intracellular location of scFv M16. In summary, we have created pH-dependent antibodies, e.g., a single chain-antibody, M16, which bind TfR with high affinity at pH7.4, and dissociate from TfR at pH 5.5 thereby markedly increasing intracellular accumulation, and potential therapeutic relevance. It is also anticipated that these antibodies will prove useful in understanding pH-dependent mechanisms underlying TfR-targeted antibody endocytosis and trafficking.

REFERENCES

1. Edgcomb S P, Murphy K P (2002) Variability in the pKa of histidine side-chains correlates with burial within proteins. Proteins: Structure, Function, and Bioinformatics 49: 1-6.
2. Chan P, Warwicker J (2009) Evidence for the adaptation of protein pH-dependence to subcellular pH. BMC Biology 7: 69.
3. Roopenian D C, Akilesh S (2007) FcRn: the neonatal Fc receptor comes of age. Nat Rev Immunol 7: 715-725.
4. Dall'Acqua W F, Woods R M, Ward E S, Palaszynski S R, Patel N K, et al. (2002) Increasing the Affinity of a Human IgG1 for the Neonatal Fc Receptor: Biological Consequences. The Journal of Immunology 169: 5171-5180.
5. Dall'Acqua W F, Kiener P A, Wu H (2006) Properties of Human IgG1s Engineered for Enhanced Binding to the Neonatal Fc Receptor (FcRn). Journal of Biological Chemistry 281: 23514-23524.
6. Oganesyan V, Damschroder M M, Woods R M, Cook K E, Wu H, et al. (2009) Structural characterization of a human Fc fragment engineered for extended serum half-life. Molecular Immunology 46: 1750-1755.
7. Vaccaro C, Zhou J, Ober R J, Ward E S (2005) Engineering the Fc region of immunoglobulin G to modulate in vivo antibody levels. Nat Biotech 23: 1283-1288.
8. Igawa T, Ishii S, Tachibana T, Maeda A, Higuchi Y, et al. (2010) Antibody recycling by engineered pH-dependent antigen binding improves the duration of antigen neutralization. Nat Biotech 28: 1203-1207.
9. Chaparro-Riggers J, Liang H, DeVay R M, Bai L, Sutton J E, et al. (2012) Increasing Serum Half-life and Extending Cholesterol Lowering in Vivo by Engineering Antibody with pH sensitive Binding to PCSK9. Journal of Biological Chemistry 287: 11090-11097.
10. Sarkar C A, Lowenhaupt K, Horan T, Boone T C, Tidor B, et al. (2002) Rational cytokine design for increased lifetime and enhanced potency using pH-activated [ldquo]histidine switching[rdquo]. Nat Biotech 20: 908-913.
11. Yoon D J, Chu D S H, Ng C W, Pham E A, Mason A B, et al. (2009) Genetically engineering transferrin to improve its in vitro ability to deliver cytotoxins. Journal of Controlled Release 133: 178-184.
12. Daniels T R, Delgado T, Rodriguez J A, Helguera G, Penichet M L (2006) The transferrin receptor part I: Biology and targeting with cytotoxic antibodies for the treatment of cancer. Clinical Immunology 121: 144-158.
13. Daniels T R, Delgado T, Helguera G, Penichet M L (2006) The transferrin receptor part II: Targeted delivery of therapeutic agents into cancer cells. Clinical Immunology 121: 159-176.
14. Sun H, Cox M C, Li H, Mason A B, Woodworth R C, et al. (1998) [1H, 13C] NMR determination of the order of lobe loading of human transferrin with iron: comparison with other metal ions. FEBS Letters 422: 315-320.
15. Wally J, Halbrooks P J, Vonrhein C, Rould M A, Everse S J, et al. (2006) The Crystal Structure of Iron-free Human Serum Transferrin Provides Insight into Inter-lobe Communication and Receptor Binding. Journal of Biological Chemistry 281: 24934-24944.
16. Mayle K M, Le A M, Kamei D T (2012) The intracellular trafficking pathway of transferrin. Biochimica et Biophysica Acta (BBA)—General Subjects 1820: 264-281.
17. Leverence R, Mason A B, Kaltashov I A (2010) Non-canonical interactions between serum transferrin and transferrin receptor evaluated with electrospray ionization mass spectrometry. Proceedings of the National Academy of Sciences 107: 8123-8128.
18. Gumerov D R, Mason A B, Kaltashov I A (2003) Interlobe Communication 704 in Human Serum Transferrin: Metal Binding and Conformational Dynamics Investigated by Electrospray Ionization Mass Spectrometry. Biochemistry 42: 5421-5428.
19. Eckenroth B E, Steere A N, Chasteen N D, Everse S J, Mason A B (2011) How the binding of human transferrin primes the transferrin receptor potentiating iron release at endosomal pH. Proceedings of the National Academy of Sciences of the United States of America 108: 13089-13094.
20. Ciechanover A, Schwartz A L, Dautry-Varsat A, Lodish H F (1983) Kinetics of internalization and recycling of transferrin and the transferrin receptor in a human hepatoma cell line. Effect of lysosomotropic agents. Journal of Biological Chemistry 258: 9681-9689.
21. Luck A N, Mason A B (2013) Structure and dynamics of drug carriers and their interaction with cellular receptors: Focus on serum transferrin. Advanced Drug Delivery Reviews 65: 1012-1019.
22. Lao B J, Tsai W-L P, Mashayekhi F, Pham E A, Mason A B, et al. (2007) Inhibition of transferrin iron release increases in vitro drug carrier efficacy. Journal of Controlled Release 117: 403-412.
23. Wenning L A, Yazdi P T, Murphy R M (1998) Quantitative analysis of protein synthesis inhibition and recovery in CRM107 immunotoxin-treated HeLa cells. Biotechnology and Bioengineering 57: 484-496.
24. Yazdi P T, Murphy R M (1994) Quantitative Analysis of Protein Synthesis Inhibition by Transferrin-Toxin Conjugates. Cancer Research 54: 6387-6394.

25. Yazdi P T, Wenning L A, Murphy R M (1995) Influence of Cellular Trafficking on Protein Synthesis Inhibition of Immunotoxins Directed against the Transferrin Receptor. Cancer Research 55: 3763-3771.
26. Boder E T, Wittrup K D (1997) Yeast surface display for screening combinatorial polypeptide libraries. Nat Biotechnol 15: 553-557.
27. Wentz A E, Shusta E V (2007) A Novel High-Throughput Screen Reveals Yeast Genes That Increase Secretion of Heterologous Proteins. Applied and Environmental Microbiology73: 1189-1198.
28. Shusta E V, Raines R T, Pluckthun A, Wittrup K D (1998) Increasing the secretory capacity of *Saccharomyces cerevisiae* for production of single-chain antibody fragments. Nat Biotech 16: 773-777.
29. Piatesi A, Howland S W, Rakestraw J A, Renner C, Robson N, et al. (2006) Directed evolution for improved secretion of cancer-testis antigen NY-ESO-1 from yeast. Protein Expression and Purification 48: 232-242.
30. Hackel B J, Huang D, Bubolz J C, Wang X X, Shusta E V (2006) Production of soluble and active transferrin receptor-targeting single-chain antibody using *Saccharomyces cerevisiae*. Pharm Res 23: 790-797.
31. Poul M-A, Becerril B, Nielsen U B, Morisson P, Marks J D (2000) Selection of tumor-specific internalizing human antibodies from phage libraries. Journal of Molecular Biology 301: 1149-1161.
32. Van Antwerp J J, Wittrup K D (2000) Fine Affinity Discrimination by Yeast Surface Display and Flow Cytometry. Biotechnology Progress 16: 31-37.
33. Tillotson B J, de Larrinoa I F, Skinner C A, Klavas D M, Shusta E V (2013) Antibody affinity maturation using yeast display with detergent-solubilized membrane proteins as antigen sources. Protein Engineering Design and Selection 26: 101-112.
34. Benatuil L, Perez J M, Belk J, Hsieh C-M (2010) An improved yeast transformation method for the generation of very large human antibody libraries. Protein Engineering Design and Selection 23: 155-159.
35. Swers J S, Kellogg B A, Wittrup K D (2004) Shuffled antibody libraries created by in vivo homologous recombination and yeast surface display. Nucleic Acids Research 32: e36-e36.
36. Gietz R D, Schiestl R H (2007) High-efficiency yeast transformation using the LiAc/SS carrier DNA/PEG method. Nat Protocols 2: 31-34.
37. Wang X X, Cho Y K, Shusta E V (2007) Mining a yeast library for brain endothelial cell-binding antibodies. Nat Methods 4: 143-145.
38. Dautry-Varsat A, Aaron C, Lodish H F (1983) pH and the Recycling of Transferrin during Receptor-Mediated Endocytosis. Proceedings of the National Academy of Sciences of the United States of America 80: 2258-2262.
39. Murtaugh M L, Fanning S W, Sharma T M, Terry A M, Horn J R (2011) A combinatorial histidine scanning library approach to engineer highly pH-dependent protein switches. Protein Sci 20: 1619-1631.
40. Chitambar C R, Zivkovic Z (1989) Release of soluble transferrin receptor from the surface of human leukemic HL60 cells. Blood 74: 602-608.
41. Gera N, Hill A B, White D P, Carbonell R G, Rao B M (2012) Design of pH sensitive binding proteins from the hyperthermophilic Sso7d scaffold. PLoS ONE 7: e48928.
42. Kulkarni M V, Tettamanzi M C, Murphy J W, Keeler C, Myszka D G, et al. (2010) Two Independent Histidines, One in Human Prolactin and One in Its Receptor, Are Critical for pH-dependent Receptor Recognition and Activation. Journal of Biological Chemistry 285: 38524-38533.
43. Martin W L, West Jr A P, Gan L, Bjorkman P J (2001) Crystal Structure at 2.8 Å of an FcRn/Heterodimeric Fc Complex: Mechanism of pH-Dependent Binding. Molecular Cell 7: 867-877.
44. Giannetti A M, Halbrooks P J, Mason A B, Vogt T M, Enns C A, et al. (2005) The molecular mechanism for receptor-stimulated iron release from the plasma iron transport protein transferrin. Structure 13: 1613-1623.
45. Schröter C, Günther R, Rhiel L, Becker S, Toleikis L, et al. (2014) A generic approach to engineer antibody pH-switches using combinatorial histidine scanning libraries and yeast display. mAbs 7: 138-151.
46. Traxlmayr M W, Lobner E, Hasenhindl C, Stadlmayr G, Oostenbrink C, et al. (2014) Construction of pH-sensitive Her2-binding IgG1-Fc by directed evolution. Biotechnology Journal 9: 1013-1022.
47. Sade H, Baumgartner C, Hugenmatter A, Moessner E, Freskgård P-O, et al. (2014) A Human Blood-Brain Barrier Transcytosis Assay Reveals Antibody Transcytosis Influenced by pH-Dependent Receptor Binding. PLoS ONE 9: e96340.
48. Atwal J K, Chen Y, Chiu C, Mortensen D L, Meilandt W J, et al. (2011) A Therapeutic Antibody Targeting BACE1 Inhibits Amyloid-β Production in Vivo. Science Translational Medicine 3: 84ra43-84ra43.
49. Yu Y J, Zhang Y, Kenrick M, Hoyte K, Luk W, et al. (2011) Boosting Brain Uptake of a Therapeutic Antibody by Reducing Its Affinity for a Transcytosis Target. Science Translational Medicine 3: 84ra44-84ra44.
50. Bien-Ly N, Yu Y J, Bumbaca D, Elstrott J, Boswell C A, et al. (2014) Transferrin receptor (TfR) trafficking determines brain uptake of TfR antibody affinity variants. The Journal of Experimental Medicine 211: 233-244.
51. Niewoehner J, Bohrmann B, Collin L, Urich E, Sade H, et al. (2014) Increased Brain Penetration and Potency of a Therapeutic Antibody Using a Monovalent Molecular Shuttle. Neuron 81: 49-60.

We claim:

1. A pH-dependent antibody that binds an antigen at a first pH and rapidly dissociates at a second pH, wherein the antigen is a transferrin receptor (TfR), wherein the pH-dependent antibody comprises at least two consecutive histidine residues at a single complementarity determining region (CDR) and wherein the CDR is CDRH1, wherein the first pH is a physiological pH and the second pH is an endosomal pH.

2. The pH-dependent antibody of claim 1, wherein the association at the second pH versus the first pH is less than 20%.

3. The pH-dependent antibody of claim 1, wherein the pH-dependent antibody comprises at least three consecutive histidine residues.

4. The pH-dependent antibody of claim 1, where the first pH is about pH 7.4.

5. The pH-dependent antibody of claim 1, where the second pH is about pH 5.5.

6. The pH-dependent antibody of claim 1, wherein the pH-dependent antibody comprises an antibody fragment having an amino acid sequence selected from the group consisting of SEQ ID NOs 13-20 (corresponding to M4, M8, M10, M11, M16, M17, M20 and M23 respectively).

7. The pH-dependent antibody of claim 1, wherein the antibody is linked to a therapeutic agent.

8. The pH-dependent antibody of claim 7, wherein the linkage is selected from the group consisting of covalent and non-covalent linkages.

9. The pH-dependent antibody of claim 7, wherein the antibody is part of a fusion protein and wherein the therapeutic agent is a second part of the fusion protein.

10. A kit for delivering a molecule into a cell, the kit comprising a pH-dependent antibody of claim 1, wherein the antibody is a pH-dependent antibody that binds an antigen at a first pH and rapidly dissociates at a second pH, wherein the antigen is a transferrin receptor (TfR), wherein the pH-dependent antibody is bound to the molecule and the antigen of the transferrin receptor (TfR) is existing within the cell, wherein the first pH is a physiological pH and the second pH is an endosomal pH.

11. A pH-dependent antibody that binds an antigen at a first pH and rapidly dissociates at a second pH, wherein the first pH is a physiological pH and the second pH is an endosomal pH, wherein the antigen is a transferrin receptor (TfR), wherein the pH-dependent antibody comprises at least two consecutive histidine residues at a single complementarity determining region (CDR) and wherein the CDR is CDRH1, wherein the pH-dependent antibody comprises an antibody fragment having an amino acid sequence of SEQ ID NO: 17 (corresponding to M16).

12. A method of delivering a therapeutic agent into a cell, the method comprising the steps of
    (a) obtaining a pH-dependent antibody of claim 1, wherein the antibody is a pH-dependent antibody that binds an antigen at a first pH and rapidly dissociates at a second pH, wherein the antigen is a transferrin receptor (TfR);
    (b) exposing the cell to a pharmaceutically effective amount of the pH-dependent antibody; and
    (c) exposing the cell to a pharmaceutically effective amount of the therapeutic agent, wherein the molecule is delivered into the cell in an enhanced manner.

13. The method of claim 12, wherein the therapeutic agent has a molecular weight larger than 500 Da.

14. The method of claim 12, wherein the cell is exposed to the therapeutic agent at the same time as the cell is exposed to the pH-dependent antibody.

15. The method of claim 12, wherein the agent is linked to the pH-dependent antibody.

16. The method of claim 12, wherein the pH-dependent antibody is obtained when an antibody is subjected to histidine-saturation mutagenesis at a single CDR.

17. The method of claim 16, wherein the CDR is CDRH1.

18. The method of claim 12, wherein in step (b) the cell is exposed to a pharmaceutically effective amount of the pH-dependent antibody at a pH different from neutral pH.

19. The method of claim 18, wherein the method is conducted at pH 5.5.

20. The method of claim 12, wherein the cell is a cancer cell.

21. The method of claim 12, wherein the method is in vivo.

22. A method of delivering a therapeutic agent across a patient's blood brain barrier, the method comprising the steps of
    (a) obtaining a pH-dependent antibody of claim 1
    (b) exposing a patient's blood brain barrier to a pharmaceutically effective amount of the pH-dependent antibody; and
    (c) exposing the patient's blood brain barrier to a pharmaceutically effective amount of the therapeutic agent, wherein the molecule is delivered across the patient's blood brain barrier in an enhanced manner.

23. The method of claim 22, wherein the therapeutic agent has a molecular weight larger than 500 Da.

24. The method of claim 22, wherein the patient's blood brain barrier is exposed to the therapeutic agent at the same time as the barrier is exposed to the pH-dependent antibody.

25. The method of claim 22, wherein the pH-dependent antibody is obtained when an antibody is subjected to histidine-saturation mutagenesis at a single CDR.

26. The method of claim 25, wherein the CDR is CDRH1.

27. The method of claim 22, wherein in step (b) the cell is exposed to a pharmaceutically effective amount of the pH-dependent antibody at a pH different from neutral pH.

28. The method of claim 27, wherein the method is conducted at pH 5.5.

* * * * *